US012753149B2

(12) United States Patent
Poras et al.

(10) Patent No.: US 12,753,149 B2
(45) Date of Patent: Oct. 6, 2026

(54) N-FORMYLHYDROXYLAMINES AS NEPRILYSIN (NEP) INHIBITORS, IN PARTICULAR AS MIXED AMINOPEPTIDASE N (APN) AND NEPRILYSIN (NEP) INHIBITORS

(71) Applicant: PHARMALEADS, Paris (FR)

(72) Inventors: Hervé Poras, Villepreux (FR); Marie-Claude Fournie-Zaluski, Paris (FR); Bernard Roques, Paris (FR)

(73) Assignee: KOS THERAPEUTICS, INC., Raleigh, NC (US)

( * ) Notice: Subject to any disclaimer, the term of this patent is extended or adjusted under 35 U.S.C. 154(b) by 1084 days.

(21) Appl. No.: 17/625,054

(22) PCT Filed: Jul. 6, 2020

(86) PCT No.: PCT/FR2020/051190
§ 371 (c)(1),
(2) Date: Jan. 5, 2022

(87) PCT Pub. No.: WO2021/005294
PCT Pub. Date: Jan. 14, 2021

(65) Prior Publication Data

US 2022/0289668 A1 Sep. 15, 2022

(30) Foreign Application Priority Data

Jul. 5, 2019 (FR) ...................................... 1907537

(51) Int. Cl.
*C07C 259/06* (2006.01)
*A61P 25/04* (2006.01)

(52) U.S. Cl.
CPC ............ *C07C 259/06* (2013.01); *A61P 25/04* (2018.01)

(58) Field of Classification Search
CPC .......... A61P 25/04; A61P 25/22; A61P 25/24; C07C 259/06
See application file for complete search history.

(56) References Cited

U.S. PATENT DOCUMENTS

| | | | |
|---|---|---|---|
| 1,437,290 A | 11/1922 | Coolidge | |
| 4,618,708 A | 10/1986 | Roques et al. | |
| 5,200,426 A | 4/1993 | Hersh et al. | |
| 5,491,169 A | 2/1996 | Roques et al. | |
| 6,391,866 B1 | 5/2002 | Roques et al. | |
| 6,518,260 B1 | 2/2003 | Fournie-Zaluski et al. | |
| 7,323,448 B2 * | 1/2008 | Hunter .................... | A61P 31/04 514/21.91 |
| 8,247,608 B2 | 8/2012 | Roques et al. | |
| 8,466,309 B2 | 6/2013 | Fournie-Zaluski et al. | |
| 10,131,681 B2 | 11/2018 | Roques et al. | |
| 2002/0165167 A1 | 11/2002 | Hunter et al. | |
| 2007/0129310 A1 | 6/2007 | Beckett et al. | |

FOREIGN PATENT DOCUMENTS

| | | | |
|---|---|---|---|
| CA | 2797595 | * | 11/2011 |
| FR | 0510862 | A | 12/1920 |
| FR | 0604030 | A | 4/1926 |
| FR | 0853092 | A | 3/1940 |
| FR | 0855015 | A | 4/1940 |
| FR | 2518088 | A1 | 6/1983 |
| FR | 2605004 | A1 | 4/1988 |
| FR | 2651229 | A1 | 3/1991 |
| FR | 2755135 | A1 | 4/1998 |
| FR | 2777780 | A1 | 10/1999 |
| WO | WO-00/43001 | A1 | 7/2000 |
| WO | WO2001/24775 | * | 12/2001 |

OTHER PUBLICATIONS

STN (STN Aug. 25, p. 1, Published 1999) (Year: 1999).*
STN (STN p. 1, Published Dec. 2011) (Year: 2011).*
Park et al. (Reversed hydroxamate-Bearing thermolysin inhibitors mimic a high-energy intermediate along the enzyme-Catalyzed proteolytic reaction pathway, Bioorganic & Medicinal Chemistry Letters, 13(19), pp. 3161-3166, Published 2003) (Year: 2003).*
Adekoya et al. (The Thermolysin Family (M4) of Enzymes: Therapeutic and Biotechnological Potential, Chemical Biology and Drug Design, vol. 73, Issue1, pp. 7-16, Published Jan. 2009) (Year: 2009).*
International Search Report and Written Opinion for Corresponding International Application No. PCT/FR2020/051190, mailing date Oct. 16, 2020.
Preliminary Search Report for Corresponding French Application No. FR1907537 dated Feb. 28, 2020.
Meek J.L. et al. "Enkephalin Catabolismin Vitro and In Vivo", Neuropharmacology, vol. 16, pp. 151-154, (1977).
Malfroy B. et al., "High-affinity enkephalin-degrading peptidase in brian is increased after morphine" Nature, vol. 276, pp. 523-526, Nov. 30, 1978.

(Continued)

*Primary Examiner* — Andrew D Kosar
*Assistant Examiner* — Blaine G Doletski
(74) *Attorney, Agent, or Firm* — MARSHALL, GERSTEIN & BORUN LLP

(57) ABSTRACT

The present invention relates to a compound of following formula (1):

$$H—CO—N(OH)—CH_2—CH(R_1)—CO—NH—(CH_2)_n—CH(R_2)—(CH_2)_m—CO—R_3 \quad (I)$$

as well as a pharmaceutically acceptable salt and/or solvate thereof.

The present invention also pertains to a pharmaceutical composition comprising at least one compound of formula (1) and at least one pharmaceutically acceptable excipient.

The present invention also relates to the use of a compound of formula (1), or a pharmaceutically acceptable salt and/or solvate thereof, or a composition comprising it, as analgesic, anxiolytic, antidepressant or anti-inflammatory.

17 Claims, 1 Drawing Sheet

(56) References Cited

OTHER PUBLICATIONS

Roques B.P. et al., "Neutral Endopeptidase 24.11: Structure, Inhibition, and Experimental and Clinic Pharmacology" Pharmacological Reviews, vol. 45, No. 1, pp. 87-146, (1993).
Roques B.P. et al., "Novel approaches to targeting neuropeptide systems" Review, TIPS, vol. 21, pp. 475-483, Dec. 2000.
Noble et al., "Protection of endogenous enkephalin catabolismas natural approach to novel analgesic and antidepressant drugs", Expert. Opin. Ther. Targets, vol. 11, No. 2, pp. 145-149, (2007).
Wisner et al., "Human Opiorphin, a natural antinociceptive modulator of opioid-dependent pathways", PNAS, vol. 103, No. 47, pp. 17979-17984, Nov. 21, 2006.
Menendez et al., "Inhibition of osteosarcoma-induced thermal hyperalgesia in mice by the orally active dual enkephalinase inhibitor PL37. Potentiationn by gabapentin", European J. Pharmacol, (2008).
Thibault et al., "Antinociceptive and anti-allodynic effects of oral PL37, a complete inhibitor of enkephalin-catabolizing enzymes, in a rat model of peripheral neuropathic pain induced by vincristine", European. J. Pharmacol., vol. 600, pp. 71-77, (2008).
Mas Nieto et al., "Facilitation of enkephalins catabolisminhibitor-induced antinociception by drugs classically used in pain management", Neuropharmacol. vol. 41, pp. 496-506, (2001).
Valverde et al., "$\Delta^9$-*tetrahydrocannabinol releases and facilitates the effects of endogenous enkephalins: reduction in morphine withdrawl syndrome without change in rewarding effect*", Eurupean. J. Neuroscience, vol. 13, pp. 1816-1824, (2001).
Heravi M & Zadsirjan V., "Recent advances in the application of the Oppolzer camphorsultam as a chiral auxiliary", Tetrahedron: Asymmetry, vol. 25, pp. 1061-1090, (2014).
Naeslund C et al., "Enantioselective synthesis of m-carboranylalanine, a boron-rich analogue of phenylalanine", Tetrahedron, vol. 61, pp. 1181-1186, (2005).
Organic Syntheses, Coll. vol. 3, pp. 377, (1955).
Organic Syntheses, vol. 25, p. 42, (1945).
Fournie-Zaluski et al., :H. NMR Configurational Correlation for Retro-Inverso Dipeptides: Application to the Determination of the Absolute Configuration of "Enkephalinase" Inhibitors. Relationship between Stereochemistry and Enzyme Recognition, Journal of Medical Chemistry, vol. 29, pp. 751-753, (1986).
Hassner A and Alexanian V., "Direct Room Tempature Exterification of Carboxylic Acids", Tetrahedron Letters, No. 46,pp. 4475-4478, (1978).
Ripka A S et al., "Synthesis of Novel Cyclic Protease Inhibitors Using Grubbs Olefin Metathesis", Bioorganic & Medicinal Chemisitry Letters, 8, pp. 357-360, (1998).
Aubry M et al., "The use of a monoclonal antibody for the rapid purification of kidney neutral endopeptidase ("enkephalinase") solubilized in octyl glucoside", Biochem Cell Biol, vol. 65, pp. 398-404, (1987).
Goudreau N et al., "Dns-Gly-(p-$NO_2$)$_{Phe}$-βAla, a Specific Fluorogenic Substrate for Neutral Endopeptidase 24.11", Analytical Biochemistry, vol. 219, pp. 87-95, (1994).
M.C. Fournié-Zaluski, et al., "New Bidentates as Full Inhibitors of Enkephalin-Degrading Enzymes: Synthesis and Analgesic Properties", Journal of Medicinal Chemistry, vol. 28, No. (9), pp. 1158-1169, (1985).
Jung Dae Park, et al., "Reversed Hydroxamate-Bearing Thermolysin Inhibitors Mimic a High-Energy Intermediate Along the Enzyme-Catalyzed Proteolytic Reaction Pathway", Bioorganic and Medicinal Chemistry Letters, vol. 13, No. (19), pp. 3161-3166, (2003).
Kyung Joo Lee, et al., "Inhibition of Thermolysin with Nitrone-Bearing Substrate Analogs: A New Type of Thermolysin Inhibitors" Bioorganic and Medicinal Chemistry Letters, vol. 8, No. (4), pp. 323-326, (1998).
S.J. Davies, et al., "Structure-Activity Relationships of the Peptide Deformylase Inhibitor BB-3497: Modification of the P2' and P3' Side Chains", Bioorganic and Medicinal Chemistry Letters, vol. 13, No. (16), pp. 2715-2718, (2003).

* cited by examiner

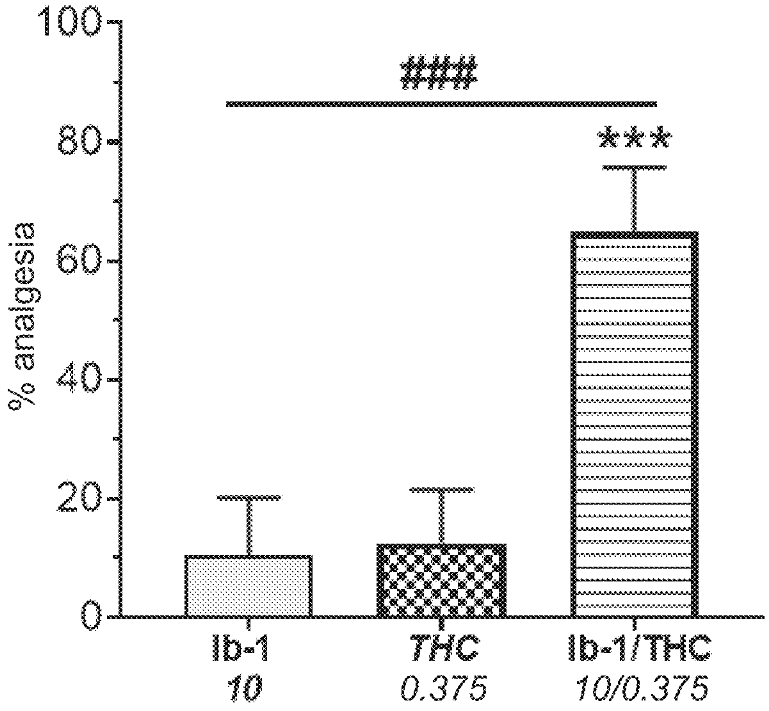
100
80
60
40
20
0
% analgesia

***
Ib-1
10
THC
0.375
Ib-1/THC
10/0.375

N-FORMYLHYDROXYLAMINES AS NEPRILYSIN (NEP) INHIBITORS, IN PARTICULAR AS MIXED AMINOPEPTIDASE N (APN) AND NEPRILYSIN (NEP) INHIBITORS

CROSS REFERENCE TO RELATED APPLICATIONS

This application is a U.S. National Stage of International Patent Application No. PCT/FR2020/051190 filed Jul. 6, 2020, which claims the benefit of priority of French Patent Application No. 1907537 filed Jul. 5, 2019, the respective disclosures of which are each incorporated herein by reference in their entireties.

FIELD OF THE INVENTION

The invention pertains to novel N-formylhydroxylamine derivatives and the use thereof as mixed neprilysin (NEP) inhibitors, and advantageously as mixed inhibitors of NEP and aminopeptidase N (APN), enzymes involved in the degradation of enkephalins, notably in the treatment of pain.

BACKGROUND OF THE INVENTION

Over the last few years, life sciences research has considerably drawn scientists to study metalloenzymes and activity modulators thereof (inhibitors and/or activators) in order to improve human health by thus selecting new therapeutic targets.

The largest category of metalloproteins is constituted of zinc enzymes. Over the last few years, substantial proof has been built up involving Zn2+ enzymes in the physiopathology and pathogenesis of a wide variety of human disorders ranging from infections to cancer.

$Zn^{2+}$ metalloproteases represent an important group of hydrolases involved in numerous physiological regulation processes such as respiration, arterial pressure, intestinal transit, the sensation of pain or the sensation of well-being, maintaining the reorganisation of the extracellular matrix at the level of joints, angiogenesis, homeostasis of proteins essential for cerebral activity, the control of hydric and caloric equilibria, etc. These enzymes are responsible, either for the maturation (formation of an active molecule from an inactive precursor), or for the inactivation (formation of inactive metabolites from an active molecule) of peptides or proteins. Thus enkephalins, peptides involved in the control of pain, may be cited, which are degraded into inactive peptides by two zinc metalloproteases, neutral aminopeptidase (APN) (Meek J. L. et al. (1977), *Neuropharmacology,* 16, 151-154) and neprilysin (NEP) (Malfroy B. et al. (1978), *Nature,* 276, 523-526). The gendral characteristic of zinc metalloproteases is the presence of at least one $Zn^{2+}$ cation, indispensable for the hydrolase activity of the enzyme. Consequently, the conventional strategy for development of efficient inhibitors of this type of enzymes consists in conceiving a molecule recognising the different bonding sub-sites of the enzyme and possessing a group having a strong affinity for $Zn^{2+}$ (review of Roques B.P. et al. (1993), *Pharmacol Rev,* 45, 87-146; Roques B.P. et al. (2000), TIPS, 21, 475-483).

The $Zn^{2+}$ ion is essential for the catalytic activity of these enzymes and is situated at the level of the active site of the enzyme, participating directly in the catalytic mechanism through an interaction with the substrate molecule undergoing transformation. The change of coordination of $Zn^{2+}$ is seemingly responsible for a change of conformation of the protein which induces an inhibition of activity of the enzyme.

Given this mechanism, the conventional structure of an inhibitor of these zinc metallo-enzymes contains a group which is a good chelator of $Zn^{2+}$ and which is capable of behaving like a monodentate or as a bidentate with respect to $Zn^{2+}$, in order to lead to enzyme-inhibitor complexes wherein the $Zn^{2+}$ will be tetra-coordinated or penta-coordinated.

Thus, compounds comprising $Zn^{2+}$ chelating groups may be envisaged as NEP enzyme inhibitors, and even advantageously as mixed APN and NEP enzyme inhibitors, which, by completely protecting the endogenous enkephalins from the enzymatic degradation thereof, thus make it possible to reveal the pharmacological activities, in particular analgesics and antidepressants, of enkephalins (Noble et al. (2007) *Expert. Opin. Ther. Targets,* 11, 145-149). Certain mixed inhibitors of these two enzymes already exist and are described in the literature, among which hydroxamates (FR2518088 and FR2605004), aminophosphinic compounds (FR2755135, FR2777780, FR0855015), amino acid derivatives with thiol function (FR2651229, FR0510862, FR0604030, FR0853092), endogenous peptides (Wisner et al. (2006), PNAS, 103, 17979-17984). These different molecules have physiochemical (solubility) and pharmacodynamic (bioavailability) properties which confer on them pharmacological efficacy by intravenous route or by oral route on different types of pain, in particular acute or chronic pain through excess nociception (Noble et al. (2007), *Expert. Opin. Ther. Targets,* 11, 145-149) and neuropathic pain (Menendez et al. (2008), *Eur J Pharmacol,* 596, 50-55; Thibault et al. (2008), *Eur. J. Pharmacol.,* 600, 71-77).

The objective of the invention is to provide compounds capable of efficiently chelating $Zn^{2+}$ ions and of interacting with the different sub-sites of NEP enzymes, and in an advantageous manner also capable of interacting with the enzymatic sub-sites of APN and having the beneficial properties of morphine substances in particular analgesia, behavioural effects (reduction in the emotional component of pain and anti-depressive responses) without their drawbacks (addiction, physical and psychic dependency, respiratory depression, constipation). Furthermore, it would be advantageous that the compounds have beneficial peripheral effects (anti-inflammatory and neuropathic pain) without the aforementioned drawbacks.

DESCRIPTION OF THE INVENTION

The invention pertains to compounds having the following generic formula (I):

$$H-CO-N(OH)-CH_2-CH(R_1)-CO-NH-(CH_2)_n-CH(R_2)-(CH_2)_m-CO-R_3 \quad (I)$$

wherein $R_1$ represents a linear or branched hydrocarbon group comprising from 1 to 6 carbon atoms, non-substituted or substituted by one or more groups selected from:

- an aryl, itself non-substituted or substituted by one or more groups selected from halogens such as fluorine and bromine, a phenyl group, a benzyl group, an $OR_4$ group, $R_4$ being selected from hydrogen and a linear or branched alkyl group comprising from 1 to 4 carbon atoms, and combinations thereof,
- a 5 or 6 membered heteroaryl comprising 1 or 2 heteroatoms, each heteroatom being selected from oxygen, nitrogen and sulphur,
- a 5 or 6 membered cycloalkyl, and
- a 5 or 6 membered cycloheteroalkyl comprising 1 or 2 heteroatoms, each heteroatom being selected from oxygen, nitrogen and sulphur, $R_2$ represents:

- hydrogen,
- a linear or branched hydrocarbon group comprising from 1 to 6 carbon atoms, non-substituted or substituted by one or more groups selected from:
  - a group selected from $OR_5$, $SR_5$ and $S(O)R_5$, $R_5$ being selected from hydrogen and a linear or branched alkyl group comprising from 1 to 4 carbon atoms,
  - a $CO_2R_6$ group, $R_6$ being selected from hydrogen, a linear or branched alkyl group comprising from 2 to 4 carbon atoms and a benzyl group,
  - an aryl, itself non-substituted or substituted by one or more groups selected from halogens, such as fluorine and bromine, an $OR_5$ group, $R_5$ having the same definition as above, and combinations thereof,
  - a 5 or 6 membered heteroaryl comprising 1 or 2 heteroatoms, each heteroatom being selected from oxygen, nitrogen and sulphur,
  - a 5 or 6 membered cycloalkyl, and
  - a 5 or 6 membered cycloheteroalkyl comprising 1 or 2 heteroatoms, each heteroatom being selected from oxygen, nitrogen and sulphur,
- an aryl, non-substituted or substituted by one or more groups selected from halogens, such as fluorine and bromine, an $OR_5$ group, $R_5$ having the same definition as above, and combinations thereof, or
- a heteroaryl comprising 1 or more heteroatoms, preferably 1 or 2, each heteroatom being selected from oxygen, nitrogen and sulphur, non-substituted or substituted by one or more groups selected from halogens, such as fluorine and bromine, an $OR_5$group, $R_5$ having the same definition as above, and combinations thereof, $R_3$ represents:

- an $OR_7$ group, $R_7$ being selected from
  - hydrogen,
  - a linear or branched alkyl group comprising from 2 to 6 carbon atoms,
  - a benzyl group, and
  - a $CHR_8$—$COOR_9$, $CHR_8$—O—C(=O)$R_8$ or $CHR_3$—O—C(=O)—$OR_9$ group wherein $R_a$ and $R_9$ are, independently of each other, selected from an alkyl group, an aryl group, an arylalkyl group, a cycloalkyl group, a cycloheteroalkyl group, a heteroalkyl group, a heteroaryl group and a heteroarylalkyl group, and
  - m and n are independently of each other an integer selected from 0 and 1, as well as pharmaceutically acceptable salts and/or solvates thereof.

The compounds of formula (I) of the present invention comprise a N-formyl hydroxylamine H—CO—N(OH)— function as ligand of $Zn^{2+}$, capable of behaving like a bidentate with regard to catalytic $Zn^{2+}$.

The present invention also relates to a compound of following formula (II):

$$H—CO—N(OR)—CH_2—CH(R_1)—CO—NH—(CH_2)_n—CH(R_2)—(CH_2)_m—CO—R_3 \quad (II)$$

wherein:

R represents:

- a linear or branched hydrocarbon group comprising from 1 to 6 carbon atoms non-substituted or substituted by one or more aryl groups, themselves non-substituted or substituted by one or more groups selected from aryls and linear or branched alkyl groups comprising from 1 to 4 carbons, or
- a $Si(R_{10})_3$ group, $R_{10}$ being a linear or branched alkyl group comprising from 1 to 4 carbon atoms, and $R_1$, $R_2$ and $R_3$ are such as defined above, as well as pharmaceutically acceptable salts and/or solvates thereof.

The invention also relates to compounds of formula (I) or compounds of formula (II) such as described above, providing that the R group in the compounds of formula (II) is a labile group in physiological conditions, for the use thereof as medicine, in particular as analgesic, anxiolytic, antidepressant or anti-inflammatory.

The invention also pertains to pharmaceutical compositions comprising at least one compound of formula (I) or compounds of formula (II) according to the present invention, providing that the R group in the compounds of formula (II) is a labile group in physiological conditions.

The invention also pertains to pharmaceutical compositions comprising at least one compound of formula (I) or compounds of formula (11) such as described above, providing that the R group in the compounds of formula (II) is a labile group in physiological conditions, and at least one compound selected from morphine and derivatives thereof, endocannabinoids and inhibitors of their metabolism, GABA derivatives such as gabapentin or pregabalin, duloxetine or channel inhibitors such as Nav 1.7 inhibitors.

The invention relates to the pharmaceutical compositions such as described above for the use thereof as analgesic, anxiolytic, antidepressant or anti-inflammatory.

Finally, the present invention pertains to a method for preparing a compound of formula (I) and a compound of formula (II) according to the present invention.

DESCRIPTION OF THE FIGURES

FIG. 1 illustrates the effect of intravenous coadministration of THC and compound Ib-1 solubilised in (EtOH/Tween 80/Water) (1/1/8) as vehicle in a hot plate test on mice. The grey bar corresponds to the analgesic response (10%) following the injection of the compound Ib-1 uniquely (at a level of 10 mg/kg), the checkered bar corresponds to the analgesic response (12%) following the injection of THC uniquely (at a level of 0.375 mg/kg) and the bar comprising horizontal lines corresponds to the analgesic response (65%) following the injection of the compound Ib-1 in association with the compound Ib-1 (at a level of 10 mg/kg of 1b-1 for 0.375 mg/kg of THC).

DETAILED DESCRIPTION OF THE INVENTION

Within the scope of the present invention, the expression "hydrocarbon group" designates an alkyl group, an alkenyl group or an alkynyl group such as defined hereafter. "Alkyl group" is taken to designate, within the meaning of the present invention, a saturated hydrocarbon chain, linear or branched. As an example, methyl, ethyl, propyl, isopropyl, butyl, iso-butyl, sec-butyl, tert-butyl, pentyl or hexyl groups may be cited.

"Alkenyl group" is taken to designate, within the meaning of the present invention, a hydrocarbon chain, linear or branched, comprising one or more double bonds. As an example, ethenyl, propenyl, butenyl, pentenyl or hexenyl groups may be cited.

"Alkynyl group" is taken to designate, within the meaning of the present invention, a hydrocarbon chain, linear or branched, comprising at least one triple bond. As an example, ethynyl or propynyl groups may be cited.

Within the meaning of the present invention, the hydrocarbon group advantageously comprises from 1 to 6 carbon atoms if it is an alkyl group and from 2 to 6 carbon atoms if it is an alkenyl or alkynyl group.

"Cycloalkyl" is taken to designate, within the meaning of the present invention, a saturated hydrocarbon ring advantageously comprising 5 or 6 carbon atoms, in particular the cyclohexyl or cyclopentyl group.

"Cycloheteroalkyl" is taken to designate, within the meaning of the present invention, a saturated hydrocarbon ring advantageously comprising 5 or 6 carbon atoms wherein one or more carbon atoms, advantageously 1 to 2, are each replaced by a heteroatom selected from sulphur, nitrogen and oxygen atoms.

"Heteroalkyl" is taken to designate, within the meaning of the present invention, an alkyl group such as defined above wherein one or more carbon atoms, advantageously 1 to 2, are each replaced by a heteroatom selected from sulphur, nitrogen and oxygen atoms.

"Aryl" is taken to designate, within the meaning of the present invention, an aromatic hydrocarbon group, preferably comprising from 6 to 10 carbon atoms and comprising one or more fused rings. It is advantageously a phenyl or naphthyl group, preferably a phenyl.

"Arylalkyl" is taken to designate, within the meaning of the present invention, an alkyl group such as defined above, wherein one or more hydrogen atoms, preferably 1 or 2, borne by the same carbon or by several different carbon atoms, are replaced by an aryl group such as defined above. It is advantageously a benzyl group.

"Heteroaryl" is taken to designate, within the meaning of the present invention, an aromatic group advantageously comprising 5 or 6 atoms, wherein one or more carbon atoms, advantageously 1 to 2, are each replaced by a heteroatom selected from sulphur, nitrogen and oxygen atoms. Examples of heteroaryl groups are furyl, thienyl, pyrrolyl, oxazolyl, isoxazolyl, thiazolyl, isothiazolyl, imidazolyl, pyrazolyl, oxadiazolyl, thiadiazolyl, triazolyl, tetrazolyl, pyridyl, pyridazinyl, pyrimidinyl, pyrazinyl, triazinyl, quinolyl, quinoxalyl or indolyl groups. Preferably, it is a thienyl group, as isostere of the phenyl group.

"Heteroarylalkyl" is taken to designate, within the meaning of the present invention, an alkyl group such as defined above, wherein one or more hydrogen atoms, preferably 1 or 2, borne by the same carbon or by several different carbon atoms, are replaced by a heteroaryl group such as defined above.

The term "halogen" designates chlorine, bromine, iodine and fluorine. Advantageously, it is an atom of fluorine, bromine or chlorine. Further advantageously, it is an atom of fluorine or bromine, and preferably fluorine.

"Unsaturated" is taken to designate, within the meaning of the present invention, that the hydrocarbon chain may comprise one or more unsaturation(s), advantageously one.

"Unsaturation" is taken to designate, within the meaning of the present invention, a double or a triple carbon-carbon bond (C═C or C≡C).

"Stereoisomer" is taken to designate, within the meaning of the present invention, a geometric isomer or an optical isomer.

Geometric isomers result from the different position of substituents on a double bond, which may then have a Z or E configuration.

Optical isomers notably result from the different position in space of substituents on a carbon atom comprising 4 different substituents. This carbon atom then constitutes a chiral or asymmetric centre. Optical isomers comprise diastereoisomers and enantiomers. Optical isomers which are mirror images of each other but not superimposable are designated "enantiomers". Optical isomers which are neither superimposable nor mirror images of each other are designated "diastereoisomers".

A mixture containing equal quantities of two individual enantiomer forms of opposite chirality is designated "racemic mixture".

"Chiral group" is taken to designate, within the meaning of the present invention, a group which is not superimposable on its mirror image. Such a chiral group could comprise in particular an asymmetric carbon atom, that is to say a carbon atom substituted by four different substituents (including hydrogen).

"Absolute configuration" is taken to designate, within the meaning of the present invention, the spatial arrangement of the atoms or chemical groups around the asymmetric carbon atom to which these atoms and chemical groups are bound. The two possible absolute configurations of an asymmetric carbon are noted S and R.

"Enantioselective synthesis" is taken to designate, within the meaning of the present invention, synthesis leading to a single enantiomer of the synthesised molecule being obtained.

The term "N-formylation reaction" designates a reaction in the course of which a nitrogen atom of an organic compound is substituted by a formyl —CHO group.

The term "peptide coupling agent" designates an organic reagent capable of activating the carboxylic acid function of an organic compound in order that the latter can form a peptide bond with a terminal amine function of another organic compound. The coupling agents the most commonly used include HATU ((dimethylamino)-N,N-dimethyl(3H-[1,2,3]triazolo[4,5-b]pyridin-3-yloxy)methaniminium hexafluorophosphate), TBTU (2-(1H-benzotriazole-1-yl)-1,1,3,3-tetramethylaminium tetrafluoroborate), BOP (benzotriazol-1-yloxytris(dimethylamino)phosphonium hexafluorophosphate), PyBOP (benzotriazol-1-yl-oxytripyrrolidinophosphonium hexafluorophosphate), HOBt (hydroxybenzotriazole) or carbodiimides, such as DCC (dicyclohexylcarbodiimide) and EDC (1-ethyl-3-(3-dimethylaminopropyl)carbodiimide). These coupling agents may sometimes be used in combination with others. For example, EDC is often used in combination with HOBt in peptide coupling reactions.

"Labile group in physiological conditions" is taken to designate, within the meaning of the present invention, a chemical group, generally a protective group for example a hydroxyl, amine or acid function, which will be removed in physiological conditions when they penetrate into the body.

For example, during oral administration, the acid pH of the stomach would be responsible for the deprotection of said labile group.

The compounds of the invention may be in the form of pharmaceutically acceptable salts, or a solvate thereof. In the present invention, "pharmaceutically acceptable" is taken to designate that which is useful in the preparation of a pharmaceutical composition which is generally safe, non-toxic and which is acceptable for veterinary use as well as human pharmaceutical use.

"Pharmaceutically acceptable salts" of a compound is taken to designate salts that are pharmaceutically acceptable, as defined here, and which have the desired pharmacological activity of the parent compound. Such salts comprise:

(1) pharmaceutically acceptable addition salts formed with bases, and (2) hydrates and solvates thereof.

Typically, the compounds of formula (I) are in the form of addition salts obtained with pharmacologically acceptable organic or inorganic bases or with a metal ion, such as an alkaline or alkaline-earth metal ion. Organic bases are for example diethanolamine, ethanolamine, N-methylglucamine, triethanolamine and tromethamine. Inorganic bases are for example aluminium hydroxide, calcium hydroxide, potassium hydroxide, sodium carbonate and sodium hydroxide. The solvates acceptable for the therapeutic use of the compounds of the invention comprise conventional solvates such as those formed during the final step of the preparation of the compounds on account of the potential presence of solvents. For example, they may be solvates due to the presence of water (which are called hydrates) or ethanol. The solvate is preferably an alcoholate, such as an ethanolate.

Preferably, the compounds of the invention are in the form of sodium salts or a hydrate thereof.

$R_1$ advantageously represents a linear or branched hydrocarbon group comprising from 1 to 6 carbon atoms substituted by one or more groups selected from:

- an aryl, itself non-substituted or substituted by one or more groups selected from halogens such as fluorine and bromine, a phenyl group, a benzyl group, an $OR_4$ group, $R_4$ being selected from hydrogen and a linear or branched alkyl group comprising from 1 to 4 carbon atoms, and combinations thereof,
- a 5 or 6 membered heteroaryl comprising 1 or 2 heteroatoms, each heteroatom being selected from oxygen, nitrogen and sulphur,
- a 5 or 6 membered cycloheteroalkyl comprising 1 or 2 heteroatoms, each heteroatom being selected from oxygen, nitrogen and sulphur.

$R_1$ advantageously represents a linear or branched hydrocarbon group comprising from 1 to 6 carbon atoms, non-substituted or substituted by an aryl, itself non-substituted or substituted by one or more groups selected from halogens such as fluorine and bromine, a phenyl group, a benzyl group, an $OR_4$ group, $R_4$ being selected from hydrogen and a linear or branched alkyl group comprising from 1 to 4 carbon atoms, and combinations thereof.

According to a preferred embodiment, $R_1$ represents a linear or branched hydrocarbon group comprising from 1 to 6 carbon atoms, substituted by an aryl, itself non-substituted or substituted by one or more groups selected from halogens such as fluorine and bromine, a phenyl group, a benzyl group, an $OR_4$ group, $R_4$ being selected from hydrogen and a linear or branched alkyl group comprising from 1 to 4 carbon atoms, and combinations thereof.

More advantageously, $R_1$ represents a hydrocarbon group, preferably a linear or branched alkyl group comprising from 1 to 6 carbon atoms, preferably 1 carbon atom, substituted by an aryl, preferably a phenyl group, itself non-substituted or substituted by a phenyl group.

According to a particular embodiment, the carbon bearing $R_1$ has an absolute configuration (R) or (S), preferably (R).

$R_2$ advantageously represents:

- hydrogen, or
- a linear or branched hydrocarbon group comprising from 1 to 6 carbon atoms, non-substituted or substituted by one or more groups selected from:
  - a group selected from $OR_5$, $SR_5$ and $S(O)R_5$, $R_5$ being selected from hydrogen and a linear or branched alkyl group comprising from 1 to 4 carbon atoms,
  - a $CO_2R_6$ group, $R_6$ being selected from hydrogen, a linear or branched alkyl group comprising from 2 to 4 carbon atoms and a benzyl group,
  - an aryl, itself non-substituted or substituted by one or more groups selected from halogens, such as fluorine and bromine, an $OR_5$ group, $R_5$ having the same definition as above, and combinations thereof,
  - a 5 or 6 membered heteroaryl comprising 1 or 2 heteroatoms, each heteroatom being selected from oxygen, nitrogen and sulphur,
  - a 5 or 6 membered cycloalkyl, and
  - a 5 or 6 membered cycloheteroalkyl comprising 1 or 2 heteroatoms, each heteroatom being selected from oxygen, nitrogen and sulphur.

According to another embodiment, $R_2$ advantageously represents:

- a linear or branched hydrocarbon group comprising from 1 to 6 carbon atoms, non-substituted or substituted by one or more groups selected from:
  - a group selected from $OR_5$, $SR_5$ and $S(O)R_5$, $R_5$ being selected from hydrogen and a linear or branched alkyl group comprising from 1 to 4 carbon atoms,
  - a $CO_2R_6$ group, $R_6$ being selected from hydrogen, a linear or branched alkyl group comprising from 2 to 4 carbon atoms and a benzyl group,
  - an aryl, itself non-substituted or substituted by one or more groups selected from halogens, such as fluorine and bromine, an $OR_5$ group, $R_5$ having the same definition as above, and combinations thereof,
  - a 5 or 6 membered heteroaryl comprising 1 or 2 heteroatoms, each heteroatom being selected from oxygen, nitrogen and sulphur,
  - a 5 or 6 membered cycloalkyl, and
  - a 5 or 6 membered cycloheteroalkyl comprising 1 or 2 heteroatoms, each heteroatom being selected from oxygen, nitrogen and sulphur,
- an aryl, non-substituted or substituted by one or more groups selected from halogens, such as fluorine and bromine, an $OR_5$ group, $R_5$ having the same definition as above, and combinations thereof, or
- a heteroaryl comprising 1 or more heteroatoms, preferably 1 or 2, each heteroatom being selected from oxygen, nitrogen and sulphur, non-substituted or substituted by one or more groups selected from halogens, such as fluorine and bromine, an ORs group, $R_5$ having the same definition as above, and combinations thereof.

According to a preferred embodiment, $R_2$ represents a linear or branched hydrocarbon group comprising from 1 to 6 carbon atoms, non-substituted or substituted by one or more groups selected from:

a group selected from $OR_5$, $SR_5$ and $S(O)R_5$, $R_5$ being selected from hydrogen and a linear or branched alkyl group comprising from 1 to 4 carbon atoms, a $CO_2R_6$ group, $R_6$ being selected from hydrogen, a linear or branched alkyl group comprising from 2 to 4 carbon atoms and a benzyl group, an aryl, itself non-substituted or substituted by one or more groups selected from halogens, such as fluorine and bromine, an $OR_5$ group, $R_5$ having the same definition as above, and combinations thereof, a 5 or 6 membered heteroaryl comprising 1 or 2 heteroatoms, each heteroatom being selected from oxygen, nitrogen and sulphur, a 5 or 6 membered cycloalkyl, and a 5 or 6 membered cycloheteroalkyl comprising 1 or 2 heteroatoms, each heteroatom being selected from oxygen, nitrogen and sulphur.

More advantageously, $R_2$ represents a hydrocarbon group, preferably an alkyl group, linear or branched comprising from 1 to 6 carbon atoms, non-substituted or substituted by one or more groups selected from:

an aryl, itself non-substituted or substituted by one or more groups selected from halogens, such as fluorine and bromine, an $OR_5$ group, $R_5$ having the same definition as above, and combinations thereof, a 5 or 6 membered cycloalkyl, and a 5 or 6 membered cycloheteroalkyl comprising 1 or 2 heteroatoms, each heteroatom being selected from oxygen, nitrogen and sulphur.

In particular, $R_2$ represents a hydrocarbon group, preferably an alkyl group, linear or branched comprising from 1 to 6 carbon atoms, non-substituted or substituted by an aryl, itself non-substituted or substituted by one or more groups selected from halogens, such as fluorine and bromine, an $OR_5$ group, $R_5$ having the same definition as above, and combinations thereof.

More specifically, the radical $R_2$ represents a hydrocarbon group, preferably an alkyl group, linear or branched comprising from 1 to 6 carbon atoms, non-substituted or substituted by an aryl, itself non-substituted. Preferably, the aryl group is a phenyl group. Even more advantageously, the radical $R_2$ represents an alkyl group, linear or branched comprising from 1 to 6 carbon atoms, preferably 1 carbon atom, non-substituted or substituted by a phenyl.

According to a particular embodiment, the carbon bearing $R_2$ has an absolute configuration (R) or (S), preferably (S).

$R_3$ advantageously represents an $OR_7$ group, $R_7$ being selected from:

hydrogen, a linear or branched alkyl group comprising from 2 to 6 carbon atoms, and a benzyl group.

According to a preferred embodiment, $R_3$ represents an $OR_7$ group, $R_7$ being selected from:

hydrogen, and a linear or branched alkyl group comprising from 2 to 6 carbon atoms.

In an even more preferred manner, $R_3$ represents an OH group.

According to a particular embodiment, within the compound of formula (I), $R_1$ represents a hydrocarbon group, notably an alkyl group, linear or branched comprising from 1 to 6 carbon atoms, substituted by an aryl, preferably a phenyl, itself non-substituted or substituted by one or more groups selected from fluorine, bromine, a phenyl group, a benzyl group, an $OR_4$ group, $R_4$ being selected from hydrogen and a linear or branched alkyl group comprising from 1 to 4 carbon atoms, and combinations thereof, preferably by a phenyl group, $R_2$ represents a hydrocarbon group, preferably an alkyl group, linear or branched comprising from 1 to 6 carbon atoms, non-substituted or substituted by one or more groups selected from:

an aryl, itself non-substituted or substituted by one or more groups selected from fluorine, bromine, an ORs group, $R_e$ being selected from hydrogen and a linear or branched alkyl group comprising from 1 to 4 carbon atoms, and combinations thereof, a 5 or 6 membered heteroaryl comprising 1 or 2 heteroatoms, each heteroatom being selected from oxygen, nitrogen and sulphur, a 5 or 6 membered cycloalkyl, and a 5 or 6 membered cycloheteroalkyl comprising 1 or 2 heteroatoms, each heteroatom being selected from oxygen, nitrogen and sulphur, preferably, $R_2$ represents an alkyl group, linear or branched comprising from 1 to 6 carbon atoms, non-substituted or substituted by a phenyl, and $R_3$ represents an $OR_7$ group, $R_7$ being selected from:

hydrogen, and a linear or branched alkyl group comprising from 2 to 6 carbon atoms, preferably $R_7$ is hydrogen.

According to a particular embodiment, the compound of formula (I) according to the present invention is a compound wherein:

$R_1$=(R)—$CH_2$Ph; $R_2$=(S)—$CH_3$; $R_3$=OH; n=m=0;
$R_1$=(S)—$CH_2$Ph; $R_2$=(S)—$CH_3$; $R_3$=OH; n=m=0;
$R_1$=(R)—$CH_2$Ph; $R_2$=(S)—$CH_2$Ph; $R_3$=OH; n=m=0;
$R_1$=(S)—$CH_2$Ph; $R_2$ '$_2$ (S)—$CH_2$Ph; $R_3$=OH; n=m=0;
$R_1$=(R)—$CH_2$Ph; $R_2$=(S)—$CH_2$Ph; $R_3$=OH; n=0; m=1;
$R_1$=(S)—$CH_2$Ph; $R_2$=(S)—$CH_2$Ph; $R_3$=OH; n=0; m=1;
$R_1$=(R)—$CH_2$Ph-4-Ph; $R_2$=(S)—$CH_3$; $R_3$=OH; n=m=0;
$R_1$=(S)—$CH_2$Ph-4-Ph; $R_2$=(S)—$CH_3$; $R_3$=OH; n=m=0;
$R_1$=(S)—$CH_2$Ph; $R_2$=(S)—$CH_2$Ph; $R_3$=OH; n=1; m=0;
$R_1$=(R)—$CH_2$Ph; $R_2$=(S)—$CH_2$Ph; $R_3$=OH; n=1; m=0, or a pharmaceutically acceptable salt and/or a solvate thereof.

In a preferred manner, the compound of the invention is $R_1$=(R)—$CH_2$Ph; $R_2$=(S)—$CH_3$; $R_3$=OH; n=m=0;
$R_1$=(R)—$CH_2$Ph; $R_2$=(S)—$CH_2$Ph; $R_3$=OH; n=m=0;
$R_1$=(R)—$CH_2$Ph; $R_2$=(S)—$CH_2$Ph; $R_3$=OH; n=0; m=1;
$R_1$=(R)—$CH_2$Ph-4-Ph; $R_2$=(S)—$CH_3$; $R_3$=OH; n=m=0;
$R_1$=(R)—$CH_2$Ph; $R_2$=(S)—$CH_2$Ph; $R_3$=OH; n=1; m=0, The present invention also relates to a compound of following formula (II):

$$H—CO—N(OR)—CH_2—CH(R_1)—CO—NH—(CH_2)—CH(R_2)—(CH_2)_m—CO—R_3 \quad (II)$$

wherein:

R represents:

a linear or branched hydrocarbon group comprising from 1 to 6 carbon atoms, non-substituted or substituted by one or more aryl groups, themselves non-substituted or substituted by one or more groups selected from aryls and linear or branched aryl groups comprising from 1 to 4 carbons, or a $Si(R_{10})_3$ group, $R_{10}$ being a linear or branched alkyl group comprising from 1 to 4 carbon atoms, and $R_1$, $R_2$, $R_3$, m and n are such as defined above.

Preferably, R represents a linear or branched alkyl group comprising from 1 to 6 carbon atoms, non-substituted or substituted by an aryl group, preferably a phenyl, or R represents a $Si(R_{10})_3$ group, $R_{10}$ being preferably a methyl. In a more preferred manner, R represents a benzyl group.

When R is a labile chemical group such as defined previously, the compound (II) is transformed, into compound (I) when it penetrates into the body under the action of the physiological conditions suited to the deprotection of the R group. The compound (II) then constitutes a prodrug of the compound (1).

The compounds of the present invention of formula (I) or formula (II), providing that the R group is a labile group under physiological conditions, may be used as medicine. More specifically, these compounds may be employed to prepare pharmaceutical compositions comprising as active ingredient at least one of the compounds described above in combination with at least one pharmaceutically acceptable excipient. Said excipients are chosen according to the desired pharmaceutical form and mode of administration from among the normal excipients which are known to those skilled in the art.

The compounds of the present invention inhibiting jointly the enzymatic activities responsible for the degradation of enkephalins, they increase their extracellular endogenous levels and turn out to be in this respect efficient analgesics and/or antidepressants. The analgesic effects of the compounds manifest themselves on various types of pain, acute or chronic, such as the post-operatory, cancerous, traumatological pain, headaches, migraines, visceral, neurogenic, neuropathic, neuro-anti-inflammatory, nociceptive pain or general pain such as fibromyalgia. Examples of pain include mechanical pain (for example muscular pain, vascular ischemia), pain caused by shingles, cancerous pain linked to the cancer itself or to the consequences of treatments, pain associated with anti-inflammatory or degenerative diseases (for example, arthritis, rheumatoid arthritis, osteoarthritis, gout), pain linked to type 1 and 2 diabetes, pain linked to migraines, facial neuralgia, headaches, pain linked to disorders of the peripheral nerves, dorsal-lumbar neuralgia, cervical-brachial, dental pain, pain linked to burns, sunburn, bites or stings, pain linked to infections, metabolic disorders (diabetes, alcoholism), nerve compressions (slipped discs, carpal tunnel, fibrosis, etc.), fractures, burns, haematomas, cuts and inflammations, visceral pain (intestinal, caused by anti-inflammatory diseases of the intestine and functional intestinal disorders, by urinary cholecystitis, such as renal colic, cystitis, genital, such as dysmenorrhea, cystitis, cardiac endometriosis, such as myocardial infarction pain).

Finally, typically, and advantageously, the compounds of the present invention do not have the major drawbacks of morphine based substances (tolerance, physical dependency, respiratory depression; nausea, sedation, constipation, etc.).

Thus, the compounds of the present invention of formula (I) or formula (II), providing that the R group is a labile group under physiological conditions and the pharmaceutical compositions containing it may be useful for at least one use selected from the following uses: analgesic, anxiolytic, antidepressant or anti-inflammatory.

The present invention also relates to the use of compounds of formula (I) or formula (II), such as defined above, provided that the R group is a labile group under physiological conditions and the pharmaceutical compositions containing it for the production of a analgesic, anxiolytic, antidepressant or anti-anti-inflammatory medicine, more specifically a medicine intended for the treatment of pain. The pain may notably be chronic or acute pain such as defined above.

The present invention also relates to a method for treating pain, notably chronic or acute pain such as defined above, comprising the administration to a patient having need of an effective dose of the compound of formula (I) or formula (II) according to the invention, providing that the R group is a labile group under physiological conditions or a pharmaceutically acceptable salt and/or solvate thereof or a composition according to the invention, preferably by parenteral route, oral route or nasal route.

In the present invention, the patient (suffering from pain, notably chronic or acute pain such as defined above) is typically an animal, preferably a mammal, advantageously it is a human.

The compounds of the present invention may be used alone or in combination with compounds known for the antinociceptive properties thereof. This combination may enable potentialisation of the pharmacological effects, especially since known antinociceptive compounds generally have undesirable secondary effects at strong doses.

Such potentialisations (synergies) of pharmacological effects have been demonstrated in the past by combining mixed inhibitors having a chemical structure different from that of the mixed inhibitors of the present invention with known antinociceptive compounds. Thus, strong potentialisation of antinociceptive responses was obtained, for example, by combination with: morphine (Mas Nieto et al. (2001), *Neuropharmacol.* 41, 496-506, THC (Valverde et al. (2001), *Eur. J. Neurosci.*, 13, 1816-1824), gabapentin (Menendez et al. (2007), *Eur. J. Pharmacol.*, 596, 50-55) and analogues thereof such as pregabalin. These associations make it possible, for an equivalent pharmacological effect, to reduce by 3 to 10 times the doses of the components of the association (morphine and inhibitor for example).

Thus, in an embodiment, the pharmaceutical compositions comprise as active ingredient at least one of the compounds of the present invention in combination with at least one antinociceptive and at least one pharmaceutically acceptable excipient. The antinociceptives may be selected from:

- morphine and derivatives thereof,
- endocannabinoids and inhibitors of their metabolism, $\Delta^9$ THC, synthetic cannabinoid receptor agonists or anandamide degradation inhibitors (FAAH),
- GABA derivatives, such as gabapentin or pregabalin,
- duloxetine, serotonin and noradrenaline reuptake inhibitor, or
- channel inhibitors such as Nav 1.7 inhibitors.

According to an embodiment, the pharmaceutical compositions of the present invention comprise as active ingredient at least one of the compounds of the present invention in combination with THC: In another embodiment, the present invention relates to a kit comprising:

a) a first composition comprising at least one compound of formula (I) or formula (II), such as defined above, providing that the group R is a labile group under physiological conditions, and b) a second composition comprising at least one other active ingredient, notably an analgesic, selected from morphine and derivatives thereof, endocannabinoids and inhibitors of their metabolism, GABA derivatives, such as gabapentin or pregabalin, duloxetine or channel inhibitors such as Nav 1.7 inhibitors, as combination product for simultaneous use, separate use or staggered over time use.

The kit according to the present invention is notably used as analgesic, anxiolytic, antidepressant or anti-inflammatory, in particular for the treatment of pain, typically chronic or acute pain such as defined above.

The pharmaceutical compositions according to the invention may be administered by parenteral route, such as by intravenous or intradermic route, or by topical, oral or nasal route.

Administrable forms by parenteral route comprise aqueous suspensions, isotonic saline solutions or sterile and injectable solutions which may contain dispersion agents and/or pharmacologically compatible wetting agents. Administrable forms by oral route comprise tablets, soft or hard capsules, powders, pills, oral solutions and suspensions. Administrable forms by nasal route comprise aerosols. Administrable forms by topical route include patches, gels, creams, ointments, lotions, sprays, eye drops.

The effective dose of a compound of the invention varies as a function of numerous parameters such as, for example, the chosen administration route, the weight, the age, the sex, the state of advancement of the pathology to treat and the sensitivity of the individual to treat.

The present invention also relates to a method for preparing a compound of formula (I) and a compound of formula (II) according to the present invention, said method comprising the following successive steps:

(a) reaction of a compound of following formula (111):

$$H—CO—N(OR)—CH_2—CH(R_1)—C(O)OH \quad (III),$$

with a compound of following formula (IV):

$$H_3N^+—(CH_2)_n—CH(R_2)—(CH_2)_m—C(O)R_3 \quad (IV)$$

wherein R, $R_1$, $R_2$, $R_3$, n and m are such as defined above, in the presence of a peptide coupling agent, such as TBTU, HATU, EDC, HOBt, BOP, PyBOP, DCC or combinations thereof, leading to the formation of a compound of formula (II) such as defined above, (b) deprotection of the compound of formula (II) derived from step (a) to lead to a compound of formula (I).

The compounds of formula (I) have potentially from 1 to 3 asymmetry centres. The radicals $R_1$, $R_2$ and $R_3$ will typically be introduced in such a way as to obtain optically pure sequences corresponding to a stereochemistry recognised for interactions with the active sites of the enzymes concerned.

Step (a):

According to a particular embodiment, the compound of formula II may be obtained by means of the following synthesis steps:

(i-1) Reaction of an Acrylic Acid Derivative V with a Hydroxylamine VI to Lead to the Acid VII,

[Chem 1]

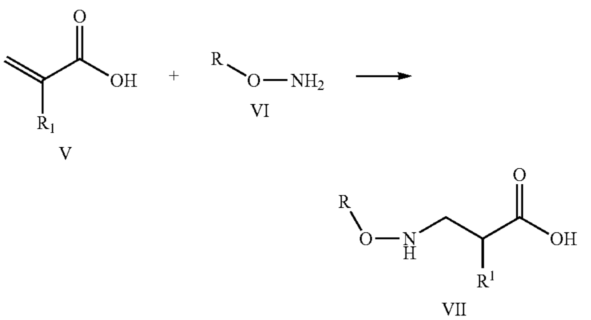

V VI VII where R and $R_1$ are such as defined previously.

Preferably, the hydroxylamine VI corresponds to benzylhydroxylamine.

(i-2)N-formylation reaction of the acid VII in formic acid in the presence of acetic anhydride to give the compound of formula III,

[Chem 2]

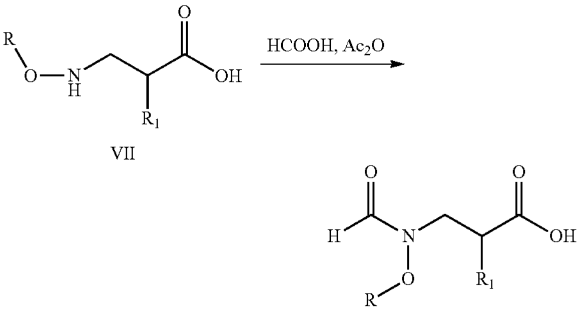

VII III

The compound III next undergoes peptide coupling with the compound of formula IV to lead to the compound of formula II:

[Chem 3]

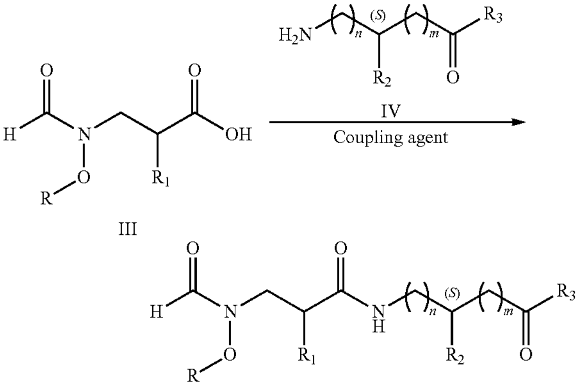

III II where R, $R_1$, $R_2$, $R_3$, n and m are such as defined above.

Preferably, the coupling agent used is TBTU. Advantageously, the reaction is carried out in the presence of DIEA (diisopropylethylamine) in an aprotic polar solvent, such as the DMF.

According to a preferred embodiment, the compound IV is enantiomerically pure. The carbon bearing the $R_2$ group has a resolved absolute configuration and advantageously corresponds to the absolute configuration (S).

According to an alternative, the method for preparing a compound of formula I comprises the following steps:

(a') reaction of a compound of formula III such as defined above with a compound of following formula VIII:

$$H_3N^+—(CH_2)_n—CH(R_2)—(CH_2)_m—C(O)OP \quad (VIII)$$

wherein $R_2$ is such as defined above and OP is a precursor of $R_3$,

P may for example be identical to R. In particular, P may be a benzyl group, leading to the formation of a compound of following formula IX:

$$H—CO—N(OR)—CH_2—CH(R_1)—CO—NH—(CH_2)_n—CH(R_2)—(CH_2)_m—C(O)—OP \quad (IX)$$

wherein R, $R_1$, $R_2$, P, n and m are such as defined above, (b') transformation of the OP group of the compound IX into a $R_3$ group such as defined above to lead to the compound of formula II or formula I such as defined above.

(c') optionally, deprotection of the compound of formula II derived from step (b') to lead to a compound of formula I.

Step (b') of transformation of the OP group precursor of $R_3$ into an $R_3$ group takes place according to methods well known to those skilled in the art. It involves, for example, a deprotection, oxidation or reduction step.

In the case where P is identical to R, the conditions of deprotection of the P group also bring about the deprotection of the amine bearing the R group and the compound of formula I is directly obtained at the end of step (b'). In which case, step (c') is not necessary. This situation arises notably when $R_3$ is equal to OH, notably when P and R are both a benzyl, removed for example by a hydrogenation reaction.

Step (b):

Step (b) corresponds to a step of deprotection of the amine bearing the OR group to lead to the compound of formula I, wherein said amine bears an OH group.

[Chem 4]

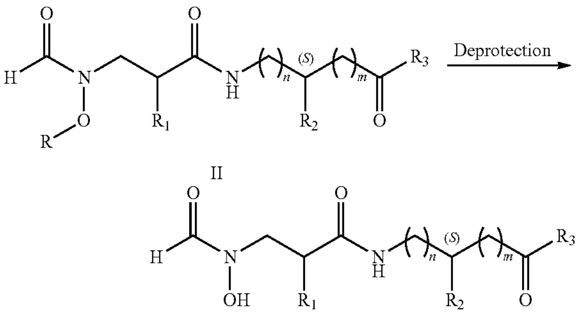

The compound I is obtained in the form of at least 2 diastereoisomers. The diastereoisomers are separated according to methods well known to those skilled in the art, typically by preparative or semi-preparative HPLC, to obtain a compound I in diastereoisomerically pure form wherein the carbons bearing $R_1$, $R_2$ and optionally $R_8$ or $R_9$ (according to the definition of $R_3$) are resolved and of respective absolute configuration optimising the properties of the compounds of the invention. In particular, the carbon bearing $R_1$ is of absolute configuration (R) or (S), preferably (R), and the carbon bearing $R_2$ is of absolute configuration (S). When it is present, the carbon bearing $R_a$ or $R_9$ is of absolute configuration (R) or (S).

Thus, in a preferential manner, the compound of formula I may correspond to the following two diastereoisomers:

[Chem 5]

I-1

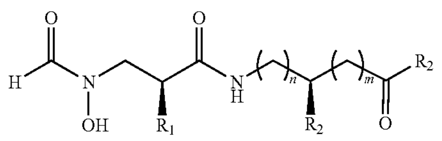

and

-continued

[Chem 6]

I-2

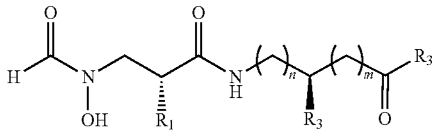

wherein $R_3$ preferably represents OH.

Enantioselective Synthesis

The compounds of formula (II) may also be synthesised in an enantioselective manner by means of Oppolzer's auxiliary (Heravi M & Zadsirjan V (2014), *Tetrahedron: Asymmetry,* 1061-1090) according to the following steps:

1° The acrylic acid derivative V reacts with thionyl chloride $SOCl_2$ to lead to the acid chloride X:

[Chem 7]

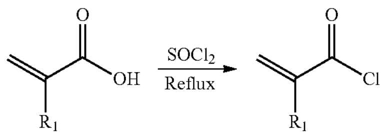

V X

2° The acid chloride X is next coupled to Oppolzer's auxiliary ((1R)-(+)-2.10-Camphorsultam) in the presence of a strong base to give the compound XI:

[Chem 8]

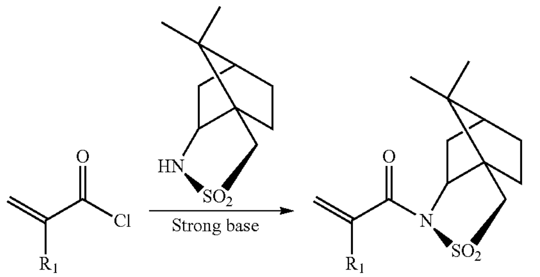

X XI

3° The stereoselective Michael addition of the hydroxylamine VI on the compound XI makes it possible to obtain in an optically pure manner the compound XII:

[Chem 9]

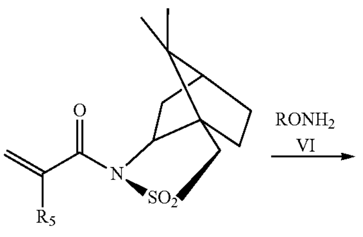

XI

-continued

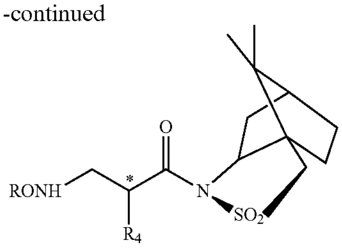

XII

4° The chiral auxiliary is cleaved by a strong base to give the optically pure compound XIII-1 (Naeslund C et al. (2005), *Tetrahedron,* 61, 1181-1186):

[Chem 10]

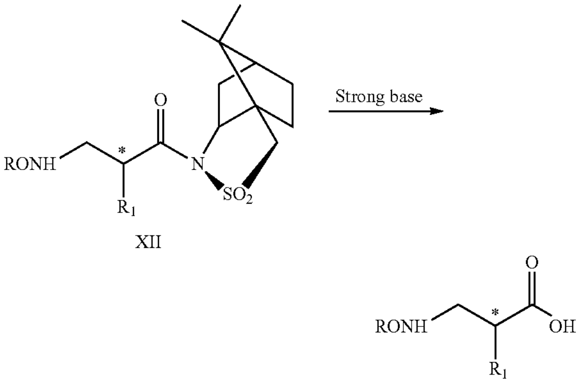

XII

XIII-1

5° The synthesis steps leading to the compounds III-1 and II-1 are identical to those used for the synthesis of racemic products, described previously.

Examples

The invention will be further illustrated without in any way being limited by the examples hereafter.

LIST OF ABBREVIATIONS $Ac_2O$: Acetic anhydride
AcOEt: Ethyl acetate
Bn: Benzyl
DIEA: Diisopropylethylamine
DMF: Dimethyl formamide
DMSO: Dimethyl sulphoxide
HPLC: High performance liquid chromatography
Ph: Phenyl
Yd: Yield
NMR: Nuclear magnetic resonance
Rt: Retention time
TFA: Trifluoroacetic acid

Synthesis of the Compounds of the Invention

The acrylic acids V are commercially available or instead synthesised as described in *Organic Syntheses*, (1955) *coll. Vol.* 3, p.377; (1945) *vol.* 25, p.42.

The absolute configuration of the carbon bearing $R_1$ was defined after separation of the 2 diastereoisomers Ia and analysis by NMR of the proton of the chemical displacement of the $CH_3$ group, by applying the rule established by Fournie-Zaluski et al. in *J Med Chem* (1986), 29, 751-753.

The absolute configuration attributed to the compound Ia-1 is thus (2R, 3S) and that of the compound Ia-2 is (2S, 3S). The absolute configurations of the analogues were fixed by analogy of stereochemical structure of the correct diastereoisomer having the best enzymatic affinity.

Step 1: synthesis of 2-alkyl-3-(benzylamino) propanoic acids VIIa for which R=Bn

[Chem 11]

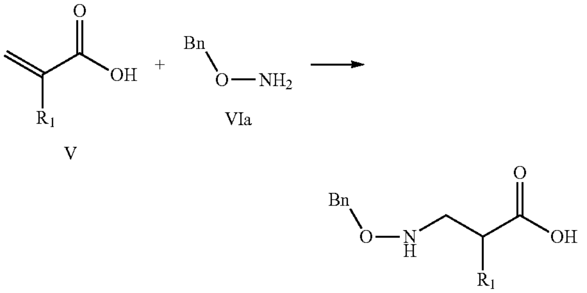

V VIa VIIa

Benzylhydroxylamine VIa (4 eq) reacts with acrylic acid V at 50° C. for 8 h. The mixture is taken up in AcOEt. Excess benzylhydroxylamine is eliminated by washing with 1N HCL. The organic phase is washed with a saturated solution of NaCl, dried on $Na_2SO_4$ and concentrated under reduced pressure. The oil is triturated in ether to give the solid compound VIIa.

VIIa-1 2-benzyl-3-(benzyloxyamino) propanoic acid $R_1=CH_2Ph$: solid, (Yd: 80.9%)

NMR (DMSO+TFA, 400 MHz): 2.7-3.3 (4H, m); 3.51 (1H, q); 4.95 (2H, s); 7.1-7.4 (10H, m)

HPLC Kromasil C18, 4.6×250 mm, $CH_3CN/H_2O$ (0.05% TFA) 6/4 Rt=7.3 min

VIIa-2 3-(benzyloxyamino)-2-(biphenyl-4-ylmethyl) propanoic acid $R_1=CH_2Ph(4-Ph)$: solid, (Yd: 87.7%)

NMR (DMSO+TFA, 400 MHz): 2.8-3.1 (3H, m); 3.25-3.35 (1H, q); 3.55 (1H, q); 4.95 (2H, s); 7.1-7.6 (14H, m)

HPLC Kromasil C18, 4.6×250 mm, $CH_3CN/H_2O$ (0.05% TFA) 7/3 Rt=8.7 min

Step 2: synthesis of 2-alkyl-3-(N-(benzyloxy)formamido) propanoic acids (IIIa, R=Bn)

[Chem 12]

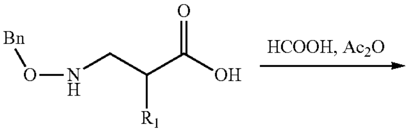

VIIa

-continued

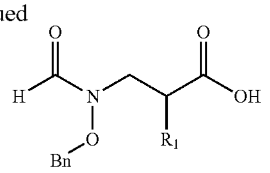

IIIa

The acid Vila is solubilised at 0° C. in formic acid. Acetic anhydride is added at 0° C. and the mixture is stirred for 3 h at 0° C. The mixture is taken up in ether then the mixture is evaporated to dryness to give the acid IIIa which is used as such for the following step.

IIIa-1 2-benzyl-3-(N-(benzyloxy)formamido) propanoic acid $R_1$=$CH_2Ph$: oil, (Yd: 100%)

NMR (DMSO+TFA, 400 MHz): 2.6-3.0 (4H, m); 3.51 (1H, q); 4.80 (2H, s); 7.1-7.4 (10H, m); 7.85 (0.5H, s), 8.15 (0.5H, s) (CHO) cis/trans HPLC Kromasil C18, 4.6×250 mm, $CH_3CN/H_2O$ (0.05% TFA) 6/4 Rt=7.2 min

IIIa-2 3-(N-(benzyloxy)formamido)-2-(biphenyl-4-ylmethyl) propanoic acid $R_1$=$CH_2Ph$(4-Ph): oil, (Yd: 100%)

NMR (DMSO+TFA, 400 MHz): 2.8-3.1 (3H, m); 3.25-3.35 (1H, q); 3.55 (1H, q); 4.95 (2H, s); 7.1-7.6 (14H, m); 7.85 (0.5H, s), 8.15 (0.5H, s) (CHO) cis/trans HPLC Kromasil C18, 4.6×250 mm, $CH_3CN/H_2O$ (0.05% TFA) 7/3 Rt=8.7 min

Step 3: amino acid coupling, synthesis of the compounds IIa

[Chem 13]

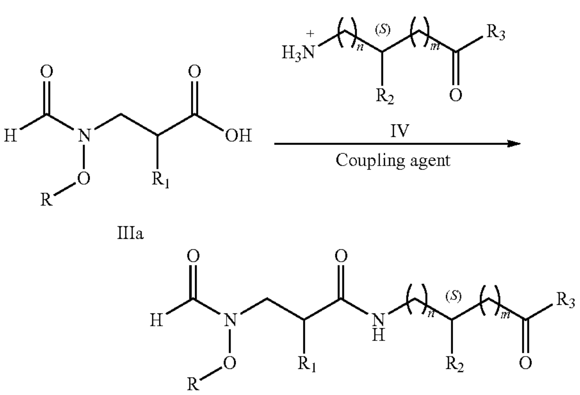

IIIa

IIa

The acid IIIa and the amino acid salt, benzylic ester (1.2 eq) IV are solubilised in DMF at 0° C. TBTU (1.2 eq) and DIEA (3 eq) are added and the mixture is stirred for 15 min at ambient temperature. The DMF is evaporated under reduced pressure and the mixture is taken up in AcOEt. The organic phase is washed with a 10% aqueous solution of citric acid, a saturated solution and is dried on $Na_2SO_4$.

The crude mixture is purified by semi-preparative HPLC on Kromasil C18 column, 21.2×250 mm with $CH_3CN/H_2O$ (0.05% TFA) 65/35 as elution system to give the compound IIa.

IIa-1 (2S)-benzyl 2-(2-benzyl-3-(N-(benzyloxy) formamido)propanamido) propanoic acid $R_1$=$CH_2Ph$, $R_2$=(S)—$CH_3$, n=m=0: solid, (Yd: 58.2%)

NMR (DMSO+TFA, 400 MHz): 1.0-1.3 (3H, m); 2.5-3.1 (3H, m); 3.15-3.60 (1H, m), 3.60 (1 H, qt); 4.25 (1H, q); 4.6-4.85 (2H, m); 515 (2H, s); 7.0-7.4 (10H, m); 7.7-8.15 (1H, m); 8.3-8.6 (1H, m)

HPLC Kromasil C18, 4.6×250 mm, $CH_3CN/H_2O$ (0.05% TFA) 7/3, Rt=151 and 16.6 min ESI (+): $[M+Na]^+$=497.35; $[(M-CH_2Ph)+Na]^+$=406.24

IIa-2 (2S)-benzyl 2-(2-benzyl-3-(N-(benzyloxy) formamido)propanamido)-3-phenyl propanoic acid $R_1$=$CH_2Ph$, $R_2$=(S)—$CH_2Ph$, n=m=0: solid, (Yd: 64.5%)

HPLC Kromasil C18, 4.6×250 mm, $CH_3CN/H_2O$ (0.05% TFA) 6/4, Rt=16.9 and 17.9 min ESI (+): $[M+Na]^+$=573.25; $[(M-CH_2Ph)+Na]^+$=482.14

IIa-3 (3S)-phenyl 3-(2-benzyl-3-(N-(benzyloxy) formamido)propanamido)-4-phenyl butanoic acid $R_1$=$CH_2Ph$, $R_2$=(S)—$CH_2Ph$, n=0; m=1: solid, (Yd: 66.5%)

HPLC Kromasil C18, 4.6×250 mm, $CH_3CN/H_2O$ (0.05% TFA) 6/4, Rt=15.2 and 16.1 min ESI (+): $[M+Na]^+$=587.26; $[(M-CH_2Ph)+Na]^+$=496.14

IIa-4 (2S)-benzyl 2-(3-(N-(benzyloxy)formamido)-2-(biphenyl-4-ylmethyl)propanamido)-propanoic acid $R_1$=$CH_2Ph$(4-Ph), $R_2$=(S)—$CH_3$, n=m=0: solid, (Yd: 59.2%)

HPLC Kromasil C18, 4.6×250 mm, $CH_3CN/H_2O$ (0.05% TFA) 7/3, Rt=16.2 and 17.2 min ESI (+): $[M+Na]^+$=497.26; $[(M-CH_2Ph)+Na]^+$=406.14

IIa-5 (2S)-phenyl 2-benzyl-3-(2-benzyl-3-(N-(benzyloxy)formamido) propanamido) propanoic acid $R_1$=$CH_2Ph$, $R_2$=(S)—$CH_2Ph$, n=1, m=0: colourless oil, (Yd: 31.0%)

HPLC Kromasil C18, 4.6×250 mm, $CH_3CN/H_2O$ (0.05% TFA) 7/3, Rt=10.6 and 11.3 min ESI (+): $[M+Na]^+$=587.26; $[(M-CH_2Ph)+Na]^+$=496.14

(S)-Alanine benzylic ester ($R_2$=(S)—$CH_3$, n=m=0), (S)-Phenyl alanine benzylic ester ($R_2$=(S)—$CH_2Ph$, n=m=0) are commercially available.

(S)-beta-Homophenylalanine benzylic ester ($R_2$=(S)—$CH_2Ph$, n=0, m=1), (R)-beta-2-Homophenylalanine benzylic ester ($R_2$=(S)—$CH_2Ph$, n=1, m=0) are produced respectively from Boc (S)-beta-Homophenylalanine and Boc (R)-beta-2-Homophenylalanine commercially available by esterification into benzylic ester and deprotection of the Boc as described in the literature and known to those skilled in the art (Hassner A and Alexanian V (1978), Tetrahedron Lett, 19, 4475; Ripka A S et al. (1998), Bioorg Med Chem Lett, 8, 357).

Step 4: Deprotection of the compound IIa and separation of the diastereoisomers I for which $R_3$ =OH

[Chem 14]

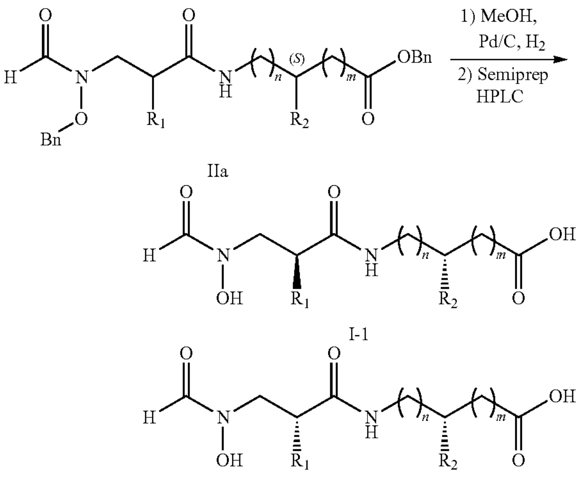

IIa

I-1

I-2

The compound IIa is solubilised in MeOH. Pd/C is added and the mixture is placed under hydrogen atmosphere for 2 h at ambient temperature. The conversion is followed by HPLC. The Pd/C is filtered on Celite. The solvent is evaporated under reduced pressure to give a mixture which is purified by semi-preparative HPLC, on Kromasil C18 column, 21.2×250 mm with $CH_3CN/H_2O$ (0.05% TFA) 35/65 as elution system to separate the 2 diastereoisomers I.

Ia-1 (S)-2-((R)-2-benzyl-3-(N-hydroxyformamido) propanamido) propanoic acid $R_1$=(R)—$CH_2Ph$, $R_2$=(S)—$CH_3$, n=m=0: solid, (Yd: 31.6%)

NMR (DMSO+TFA, 400 MHz): 1.15 (3H, t); 2.5-3.2 (4H, m); 3.35-3.70 (1H, m); 4.15 (1H, t); 7.1-7.3 (5H, m); 7.7-8.15 (1H, m) and 8.1-8.3 (1H, m) (CHO, cis/trans isomerism)

HPLC Kromasil C18, 4.6×250 mm, $CH_3CN/H_2O$ (0.05% TFA) 3/7, Rt=6.2 min Ia-2 (S)-2-((S)-2-benzyl-3-(N-hydroxyformamido)propanamido) propanoic acid $R_1$=(S)—$CH_2Ph$, $R_2$=(S)—$CH_3$, n=m=0: solid, (Yd: 23.4%)

NMR (DMSO+TFA, 400 MHz): 1.0 (3H, t); 2.5-2.75 (2H, m); 2.95 (1H, m); 3.35-3.70 (2H, m); 4.05 (1H, qt); 7.1-7.3 (5H, m); 7.8-8.25 (1H, m) and 8.05-8.2 (1H, m) (CHO, cis/trans isomerism)

HPLC Kromasil C18, 4.6×250 mm, $CH_3CN/H_2O$ (0.05% TFA) 3/7, Rt=8.5 min

Ib-1 (S)-2-((R)-2-benzyl-3-(N-hydroxyformamido) propanamido)-3-phenylpropanoic acid $R_1$=(R)—$CH_2Ph$, $R_2$=(S)—$CH_2Ph$, n=m=0: solid, (Yd: 23.0%)

NMR (DMSO+TFA, 400 MHz): 2.6-3.1 (5H, m); 3.15-3.40 (2H, m), 3.55 (1H, q); 4.40 (1H, m); 6.9-7.3 (10H, m); 7.7-8.15 (1H, m) and 8.20-8.35 (1H, m) (CHO, cis/trans isomerism)

HPLC Kromasil C18, 4.6×250 mm, $CH_3CN/H_2O$ (0.05% TEA) 35/65, Rt=12.2 min

Ib-2 (S)-2-((S)-2-benzyl-3-(N-hydroxyformamido) propanamido)-3-phenylpropanoic acid $R_1$=(S)—$CH_2Ph$, $R_2$=(S)—$CH_2Ph$, n=m=0: solid, (Yd: 29.0%)

NMR (DMSO+TFA, 400 MHz): 2.6-3.1 (5H, m); 3.15-3.40 (2H, m), 3.55 (1H, q); 4.40 (1H, m); 6.9-7.3 (10H, m); 7.7-8.15 (1H, m) and 8.10-8.35 (1H, m) (CHO, cis/trans isomerism)

HPLC Kromasil C18, 4.6×250 mm, $CH_3CN/H_2O$ (0.05% TFA) 35/65, Rt=20.5 min

Ic-1 (S)-3-((R)-2-benzyl-3-(N-hydroxyformamido) propanamido)-4-phenyl butanoic acid $R_1$=(R)—$CH_2Ph$, $R_2$=(S)—$CH_2Ph$, n=0, m=1: solid, (Yd: 35.0%)

NMR (DMSO+TFA, 400 MHz): 2.15-2.85 (7H, m); 3.15-3.40 (2H, m); 4.25 (1H, m); 6.9-7.3 (10H, m); 7.6-8.3 (2H, m) (CHO, cis/trans isomerism)

HPLC Kromasil C18, 4.6×250 mm, $CH_3CN/H_2O$ (0.05% TFA) 35/65, Rt=9.95 min

Ic-2 (S)-3-((R)-2-benzyl-3-(N-hydroxyformamido) propanamido)-4-phenyl butanoic acid $R_1$=(S)—$CH_2Ph$, $R_2$=(S)—$CH_2Ph$, n=0, m=1: solid, (Yd: 40.0%)

NMR (DMSO+TFA, 400 MHz): 2.6-3.1 (7H, m); 3.2-3.60 (2H, m); 4.15 (1H, m); 6.9-7.2 (10H, m); 7.7-8.4(2H, m) (CHO, cis/trans isomerism)

HPLC Kromasil C18, 4.6×250 mm, $CH_3CN/H_2O$ (0.05% TFA) 35/65, Rt=16.7 min

Id-1 (S)-2-((R)-3-(biphenyl-4-yl)-2-(N-hydroxyformamido)propanamido) propanoic acid $R_1$=(R)—$CH_2Ph(4-Ph)$, $R_2$=(S)—$CH_3$, n=m=0: solid, (Yd: 21.9%)

NMR (DMSO+TFA, 400 MHz): 1.15 (3H, t); 2.5-3.2 (4H, m); 3.40-3.70 (1H, m); 4.15 (1H, t); 7.1-7.5 (9H, m); 7.7-8.4(2H, m) (CHO, cis/trans isomerism)

HPLC Kromasil C18, 4.6×250 mm, $CH_3CN/H_2O$ (0.05% TFA) 4/6, Rt=9.6 min

Id-2 (S)-2-((S)-3-(biphenyl-4-yl)-2-(N-hydroxyformamido)propanamido) propanoic acid $R_1$=(S)—$CH_2Ph(4-Ph)$, $R_2$=(S)—$CH_3$, n=m=0: solid, (Yd: 29.2%)

NMR (DMSO+TFA, 400 MHz): 1.0 (3H, t); 2.5-2.75 (2H, m); 3.0 (1H, m); 3.30-3.70 (2H, m); 4.05 (1H, qt); 7.1-7.55 (9H, m); 7.7-8.4(2H, m) (CHO, cis/trans isomerism)

HPLC Kromasil C18, 4.6×250 mm, $CH_3CN/H_2O$ (0.05% TFA) 4/6, Rt=12.6 min

Ie-1 (S)-2-benzyl-3-((R)-2-benzyl-3-(N-hydroxyformamido)propanamido) propanoic acid $R_1$=(R)—$CH_2Ph$, $R_2$=(S)—$CH_2Ph$, n=1, m=0: solid, (Yd: 8.7%)

NMR (DMSO+TFA, 400 MHz): 2.15-2.85 (9H, m); 3.15-3.40 (2H, m); 7.0-7.4 (10H, m); 7.7-8.2 (2H, m) (CHO, cis/trans isomerism)

HPLC Kromasil C18, 4.6×250 mm, $CH_3CN/H_2O$ (0.05% TFA) 30/70, Rt=17.6 min

Ie-2 (S)-2-benzyl-3-((S)-2-benzyl-3-(N-hydroxyformamido)propanamido) propanoic acid $R_1$=(S)—$CH_2$Ph, $R_2$=(S)—$CH_2$Ph, n=1, m=0: solid, (Yd: 9.6%)

NMR (DMSO+TFA, 400 MHz): 2.15-2.85 (9H, m); 3.15-3.40 (2H, m); 7.05-7.35 (10H, m); 7.9-8.35 (2H, m) (CHO, cis/trans isomerism)

HPLC Kromasil C18, 4.6×250 mm, $CH_3CN/H_2O$ (0.05% TFA) 30/70, Rt=20.0 min

Chiral synthesis of the compound XIIIa-1

Step 1: synthesis of the chloride of 2-benzylacrylic acid Xa

[Chem 15]

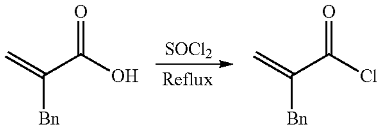

Va Xa 2-benzylacrylic acid Va (2 g, 12.3 mmol) is heated to reflux in 14 mL of thionyl chloride for 3h. Excess $SOC_2$ is evaporated under reduced pressure. A clear yellow oil is obtained in a quantitative manner and is used as such for the following step.

HPLC Kromasil C18, 4.6×250 mm, $CH_3CN/H_2O$ (0.05% TFA) 50/50, Rt=3.77 min

Step 2: Synthesis of the adduct 2-benzylacrylic acid-(1R)-(+)-2,10-Camphorsultam Xia

[Chem 16]

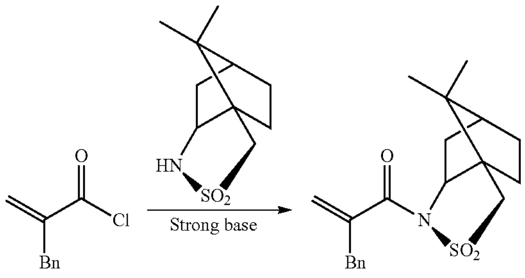

Xa XIa (1R)-(+)-2,10-Camphorsultam (19.7 g, 90.0 mmol) is solubilised in 200 mL of THF. The mixture is cooled to 0° C. and 60% NaH in oil (4.4 g, 110 mmol, 1.2 equiv) is added. The mixture is stirred for 30 min at 0° C. with formation of a salt. The acid chloride Xa (19.98 g, 110 mmol, 1.2 equiv) in solution in 100 mL of THE is added and the mixture is stirred at ambient temperature for 48 h. The THE is evaporated to dryness and the mixture is taken up in AcOEt. The organic phase is washed with 1N HCl, 10% $NaHCO_3$, $H_2O$ and a saturated solution of NaCl then it is dried on $Na_2SO_4$ then evaporated to dryness to give a white solid, the compound XIa (18.3 g, Yd: 56%), after recrystallisation in ether.

NMR ($CDCl_3$, 400 MHz): 0.8-2.0 (12H, m); 2.55 (1H, q); 3.05 (1H, d); 3.40 (1H, dd); 3.55 (1H, dd); 3.95 (1H, t); 5.30 (1H, s); 5.80 (1H, s); 7.10-7.40 (5H, m)

HPLC Kromasil C18, 4.6×250 mm, $CH_3CN/H_2O$ (0.1% TFA) 70/30, Rt=13.7 min

Step 3: Synthesis of the adduct 2-benzyl-3-(benzyloxyamino) propanoic acid -(1R)-(+)-2,10-Camphorsultam XIIa

[Chem 17]

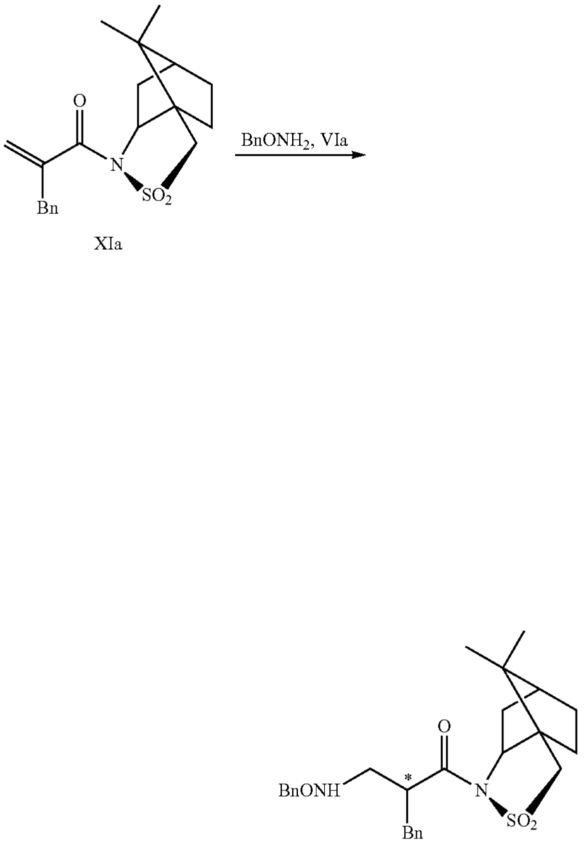

XIa

XIIa

The compound XIa (1.05 g, 2.9 mmol) is solubilised in 10 mL of $CH_2Cl_2$. Benzylhydroxylamine Via (864 mg, 7 mmol, 2.4 equiv) is added and the mixture is heated to reflux for 24 h. The mixture is diluted with $CH_2Cl_2$ and with water. The organic phase is washed with 1N HCl, $H_2O$, a saturated solution of NaCl, dried on $Na_2SO_4$ then evaporated to dryness to give 1.45 g of a colourless oil.

After crystallisation in EtOH, 790 mg of a white solid (XIIa) are obtained (Yd: 56%).

NMR (CDCs, 400 MHz): 0.8 (3H, s); 1.0 (3H, s); 1.1-1.9 (7H, m); 2.55 (1H, q); 2.95 (1H, dd); 3.05 (1H, dd); 3.15 (1H, t); 3.35 (3H, m); 3.60 (4H, m); 3.80 (1H, t); 4.45 (2H, s); 7.10-7.40 (10H, m)

HPLC Symmetry C18, 4.6×250 mm, $CH_3CN/H_2O$ (0.1% TFA) 60/40, Rt=15.0 min

Step 4: Hydrolysis of the chiral auxiliary: synthesis of 2-benzyl-3-(benzyloxyamino) propanoic acid XIIIa-1

[Chem 18]

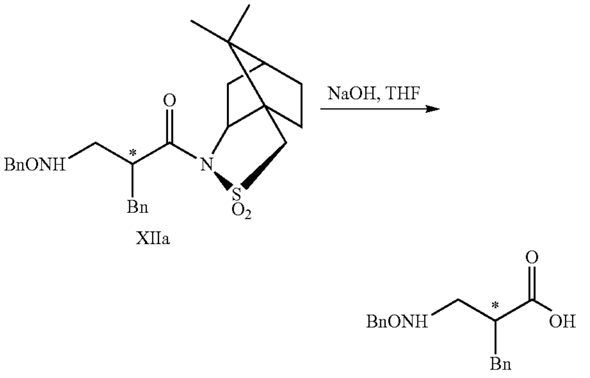

XIIa

XIIIa-1

The compound XIIa (700 mg, 1.45 mmol) is solubilised in 30 mL of THF. 6 mL of 1N LiOH are added and the mixture is stirred at 55° C. for 48 h. The mixture is acidified to pH 1-2 by 1 N HCl. The THE is evaporated to dryness and the mixture is taken up in AcOEt. The organic phase is washed with $H_2O$, a saturated solution of NaCl, dried on $Na_2SO_4$ then evaporated to dryness to give 400 mg of a slightly yellow oil. The product is purified on silica column with $CH_2Cl_2$/MeOH 9/1 as elution system to give 174 mg of the compound XIIIa-1 (Yd: 44.0%) as oil which crystallises.

NMR ($CDCl_3$, 400 MHz): 2.75 (1H, m); 2.85-3.10 (1H, q); 4.65 (2H, s); 7.1-7.4 (10H, m)

HPLC Kromasil C18, 4.6×250 mm, $CH_3CN/H_2O$ (0.1% TFA) 4/6 Rt=12.3 min

Step 5: synthesis of (2S)-benzyl 2-(2-benzyl-3-(N-(benzyloxy)formamido)propanamido) propanoic acid IIIa-1

[Chem 19]

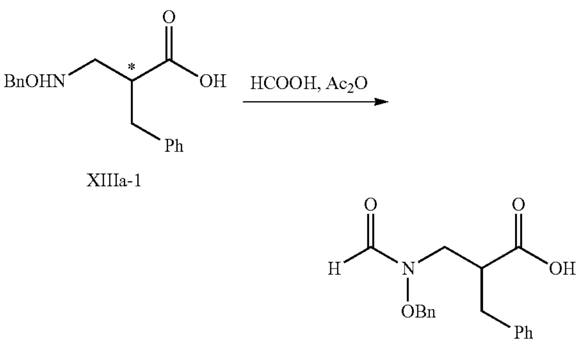

XIIIa-1

IIIa-1

The acid XIIIa-1 (12 mg, 0.042 mmol) is solubilised at 0° C. in formic acid (1 mL), Acetic anhydride (0.5 mL) is added at 0° C. and the mixture is stirred for 4 h at 0° C. The mixture is taken up in dichloromethane and water. The organic phase is washed with a saturated solution of NaCl, dried on $Na_2SO_4$ and is evaporated to dryness to give the acid IIIa-1 (13 mg, Yd: 100%) in the form of a colourless oil which is used as such for the following step.

[Chem 20]

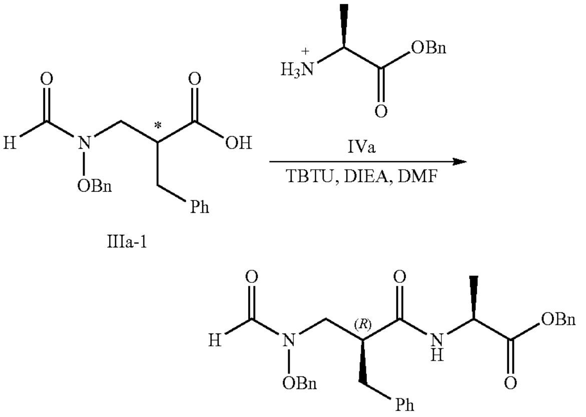

IIIa-1

IIa-1

The acid IIIa-1 (13 mg, 0.042 mmol), described previously and the salt of the benzylic ester of (S)-Alanine (11 mg, 0.054 mmol, 1.3 eq) are solubilised in 1 mL of DMF at 0° C., TBTU (12 mg, 0.052 mmol, 1.3 eq) and DIEA (22 μL, 0.126 mmol, 3 eq) are added and the mixture is stirred for 15 min at ambient temperature. The DMF is evaporated under reduced pressure and the mixture is taken up in AcOEt. The organic phase is washed with a 10% aqueous solution of citric acid, a saturated solution and is dried on $Na_2SO_4$.

The crude mixture is purified by semi-preparative HPLC on Kromasil C18 column, 21.2*250 mm with $CH_3CN/H_2O$ (0.1% TFA) 65/35 as elution system to give 3.8 mg of the compound IIa-1 (Yd=19.0%).

NMR (DMSO+TFA, 400 MHz): 1.3 (3H, t); 2.8-3.8 (5H, m); 4.25 (1H, q); 4.65-4.85 (2H, m); 5.15 (2H, s); 7.0-7.4 (10H, m); 7.7 and 8.15 (1H, m) CHO (cis/trans isomerism); 8.45-8.65 (1H, NH, m) (cis/trans isomerism)

HPLC Symmetry C18, 4.6×250 mm, $CH_3CN/H_2O$ (0.1% TFA) 6/4, Rt=11.94 (96.0% dia 2R, 3S) and 11.69 min (4.0% dia 2S, 3S)

The absolute configuration of the carbon bearing the benzyl group is defined by NMR analysis, by applying the rule established by Fournie-Zaluski et al. in J Med Chem (1986), 29, 751-753.

The absolute configuration attributed to the compound IIa-1 is thus (2R, 3S) and the enantiomeric excess obtained during the Michael addition in the presence of the chiral auxiliary is thus 96%. This chiral synthesis may also apply to the other analogues.

Measurement of Inhibitory Power

The claimed inhibitors were tested on different $Zn^{2+}$ peptidases representative of this family of enzymes, capable of inhibiting them, such as type 1 neprilysin (E.C.3.4.24.11, NEP-1), neutral aminopeptidase (E.C.3.4.11.2, APN) and LTA4H.

The assays are carried out on 99 well plates in the presence of fluorigenic substrates specific for each enzyme.

Generally speaking, the inhibitors are pre-incubated, in increasing concentrations, with the enzyme for 10 min, at 37° C. The substrate is then added and the mixture is incubated for 30 to 60 min at 37° C. The reaction is stopped at 4° C. and the reading of the fluorescence emitted is done by reading the Berthold Twinkle LS970B plate. An inhibition curve is then plotted as a function of the concentration of inhibitor using GraphPad software, then the Ki is determined from the Cheng Prusoff formula: $Ki=IC_{50}/(1+(S/Km))$.

were prepared without inhibitor. The percentage cleavage was evaluated and compared with a relative activity of 100%, and the $IC_{50}$ values were determined as a consequence. The Ki values of the inhibitors (average of at least three double independent assays) were calculated using the equation $Ki=IC_{50}/(1+[S]/Km)$.

Results: Inhibitory powers NEP, APN, LTA4H $$H-CO-N(OH)-CH_2-CH(R_1)-CO-NH-(CH_2)_nCH(R_2)(CH_2)_m-CO-R_3 \quad (1)$$

TABLE 1

| Compound | $R_1$ | $R_2$ | n, m | $R_3$ | NEP (nM) | APN (nM) | LTA4H (nM) |
|---|---|---|---|---|---|---|---|
| Ia-1 | (R)—$CH_2Ph$ | (S)—$CH_3$ | n = m = 0 | OH | 3.3 ± 0.7 | 143 ± 9 | 7.5 ± 0.4 |
| Ia-2 | (S)—$CH_2Ph$ | (S)—$CH_3$ | n = m = 0 | OH | 17.7 ± 0.9 | >10000 | nd |
| Ib-1 | (R)—$CH_2Ph$ | (S)—$CH_2Ph$ | n = m = 0 | OH | 0.5 ± 0.1 | 24.0 ± 0.4 | 26 ± 2 |
| Ib-2 | (S)—$CH_2Ph$ | (S)—$CH_2Ph$ | n = m = 0 | OH | 23.1 ± 1.1 | >10000 | nd |
| Ic-1 | (R)—$CH_2Ph$ | (S)—$CH_2Ph$ | n = 0, m = 1 | OH | 6.3 ± 0.3 | 12.0 ± 1.7 | 443 ± 75 |
| Ic-2 | (S)—$CH_2Ph$ | (S)—$CH_2Ph$ | n = 0, m = 1 | OH | 54.6 ± 2.4 | 624 ± 20 | >10000 |
| Id-1 | (R)—$CH_2Ph$-4-Ph | (S)—$CH_3$ | n = m = 0 | OH | 0.08 ± 0.01 | 86 ± 8 | 6.1 ± 0.7 |
| Id-2 | (S)—$CH_2Ph$-4-Ph | (S)—$CH_3$ | n = m = 0 | OH | 44.1 ± 2.2 | 817 ± 80 | >10000 |
| Ie-1 | (S)—$CH_2Ph$ | (S)—$CH_2Ph$ | n = 1, m = 0 | OH | 30.2 ± 2.8 | 1750 ± 20 | nd |
| Ie-2 | (R)—$CH_2Ph$ | (S)—$CH_2Ph$ | n = 1, m = 0 | OH | 2.6 ± 0.1 | 35.3 ± 3.8 | nd |

nd: non determined

Neprilysin (NEP) assay

Neprilysin, purified from rabbit kidney (Aubry M et al. (1987), Biochem Cell Biol 65, 398-404), is used at final 200 ng/mL in 50 mM Tris buffer pH. 7.4. The substrate, Dansyl-Gly-($NO_2$)Phe-ß-Ala (Goudreau N et al. (1994), *Anal Biochem,* 219, 87-95) (Km=37 μM), is dissolved in ethanol and is used at final 20 μM. Increasing concentrations (from $10^{-10}$ to $10^{-3}$ M) of inhibitors are pre-incubated for 15 min at 37° C. with NEP in 50 mM Tris buffer, pH 7.4. The substrate is next added and the incubation is continued for 60 min. The reaction is stopped by placing the plate in ice for 10 min. The reading of the fluorescence emitted is carried out in a fluorimeter at λex=355 nm, λem=535 nm.

Neutral aminopeptidase (APN) assay

The measurement of the inhibition of aminopeptidase N (APN) is carried out by use of the substrate L-Ala↓ß-NA (50 μM, Sigma Aldrich). The inhibitory powers are determined by using recombinant human enzyme (rh) (50 ng/mL; R&D System). Increasing concentrations (from $10^{-10}$ to $10^{-3}$ M) of inhibitors are pre-incubated for 30 min at 37° C. with APN-rh in 50 mM Tris buffer, pH 7.4. The substrate is next added and the incubation is continued for 30 min at 37° C. The reaction is stopped by placing the plate in ice for 10 min. The reading of the emitted fluorescence is measured in a fluorimeter at λex=340 nm, λem=405 nm.

LTA4 hydrolase assay

To determine the Ki values of the different inhibitors with regard to LTA4H, 0.6 μg/mL of recombinant enzyme were incubated beforehand for 30 minutes at 37° C. in 50 mM Tris HCl, pH 7.4, 100 mM NaCl, with increasing concentrations of inhibitor (from 10-$^{-10}$ M to $10^{-4}$ M of final concentration). The fluorescent substrate (L)-Ala-ß-naphthylamide (1 mM) is added in a final volume of 100 μL and is incubated at 37° C. for 15 minutes. The fluorescence values are measured on a Berthold Twinkle LB 970 (λex=340 nm, λem=405 nm, energy of the lamp 10000). Samples containing 0% hydrolysis were obtained by adding the substrate to the buffer and samples having a relative activity of 100%

Pharmacological Test

FIG. 1 shows that the intravenous association of THC and the compound Ib-1 at inactive doses in this test induces a considerable synergic analgesic effect, 10 min after injection, in the hot plate test on male OF1 mice.

The invention claimed is:

1. A compound of following formula (I):

$$H—CO—N(OH)—CH_2—CH(R_1)—CO—NH—(CH_2)_n—CH(R_2)—(CH_2)_m—CO—R_3 \quad (I)$$

wherein:

$R_1$ represents a linear or branched hydrocarbon group comprising from 1 to 6 carbon atoms substituted by one or more groups selected from:

an aryl, which is substituted by one or more groups selected from halogens, a phenyl group, a benzyl group, an $OR_4$ group, $R_4$ being selected from hydrogen and a linear or branched alkyl group comprising from 1 to 4 carbon atoms, and combinations thereof, a 5 or 6 membered heteroaryl comprising 1 or 2 heteroatoms, each heteroatom being selected from oxygen, nitrogen and sulphur, and a 5 or 6 membered cycloheteroalkyl comprising 1 or 2 heteroatoms, each heteroatom being selected from oxygen, nitrogen and sulphur, $R_2$ represents:

a linear or branched hydrocarbon group comprising from 1 to 6 carbon atoms, non-substituted or substituted by one or more groups selected from:

a group selected from ORS, $SR_5$ and $S(O)R_5$, $R_5$ being selected from hydrogen and a linear or branched alkyl group comprising from 1 to 4 carbon atoms, a $CO_2R_6$ group, $R_6$ being selected from hydrogen, a linear or branched alkyl group comprising from 2 to 4 carbon atoms and a benzyl group, an aryl, which is non-substituted or substituted by one or more groups selected from halogens, an $OR_5$ group, $R_5$ having the same definition as above, and combinations thereof, a 5 or 6 membered heteroaryl comprising 1 or 2 heteroatoms, each heteroatom being selected from oxygen, nitrogen and sulphur, a 5 or 6 membered cycloalkyl, and a 5 or 6 membered cycloheteroalkyl comprising 1 or 2 heteroatoms, each heteroatom being selected from oxygen, nitrogen and sulphur, an aryl, non-substituted or substituted by one or more groups selected from halogens, an $OR_5$ group, $R_5$ having the same definition as above, and combinations thereof, or a heteroaryl comprising 1 or more heteroatoms, each heteroatom being selected from oxygen, nitrogen and sulphur, non-substituted or substituted by one or more groups selected from halogens, an $OR_5$ group, $R_5$ having the same definition as above, and combinations thereof, $R_3$ represents:

an $OR_7$ group, $R_7$ being selected from:

hydrogen, a linear or branched alkyl group comprising from 2 to 6 carbon atoms, a benzyl group, and a $CHR_8$—$COOR_9$, $CHR_8$—O—C(=O)$R_9$ or $CHR_8$O—C(=O)—$OR_9$ group wherein $R_8$ and $R_9$ are, independently of each other, selected from an alkyl group, an aryl group, an arylalkyl group, a cycloalkyl group, a cycloheteroalkyl group, a heteroalkyl group, a heteroaryl group and a heteroarylalkyl group, and m and n are independently of each other an integer selected from 0 and 1, the carbon atom bearing $R_1$ having an absolute configuration (R) or (S) and the carbon atom bearing $R_2$ having an absolute configuration (S), as well as pharmaceutically acceptable salts and/or solvates thereof.

2. The compound according to claim 1, wherein $R_1$ represents a linear or branched hydrocarbon group comprising from 1 to 6 carbon atoms, substituted by an aryl, which is substituted by one or more groups selected from halogens, a phenyl group, a benzyl group, an $OR_4$ group, $R_4$ being selected from hydrogen and a linear or branched alkyl group comprising from 1 to 4 carbon atoms, and combinations thereof.

3. The compound according to claim 1, wherein $R_2$ represents a linear or branched hydrocarbon group comprising from 1 to 6 carbon atoms, non-substituted or substituted by one or more groups selected from:

an aryl, which is non-substituted or substituted by one or more groups selected from halogens such as fluorine and bromine, an $OR_5$ group, $R_5$ having the same definition as in claim 1, and combinations thereof, a 5 or 6 membered cycloalkyl, and a 5 or 6 membered cycloheteroalkyl comprising 1 or 2 heteroatoms, each heteroatom being selected from oxygen, nitrogen and sulphur.

4. The compound according to claim 1, wherein $R_3$ represents an $OR_7$ group, $R_7$ being selected from:

hydrogen, and a linear or branched alkyl group comprising from 2 to 6 carbon atoms.

5. The compound according to claim 1, wherein:

$R_1$ represents a linear or branched hydrocarbon group comprising from 1 to 6 carbon atoms, substituted by an aryl, which is substituted by one or more groups selected from fluorine, bromine, a phenyl group, a benzyl group, an $OR_4$ group, $R_4$ being selected from hydrogen and a linear or branched alkyl group comprising from 1 to 4 carbon atoms, and combinations thereof, $R_2$ represents a linear or branched hydrocarbon group comprising from 1 to 6 carbon atoms, non-substituted or substituted by one or more groups selected from:

an aryl, which is non-substituted or substituted by one or more groups selected from fluorine, bromine, an $OR_5$ group, $R_5$ having the same definition as claim 1, and combinations thereof, a 5 or 6 membered heteroaryl comprising 1 or 2 heteroatoms, each heteroatom being selected from oxygen, nitrogen and sulphur, a 5 or 6 membered cycloalkyl, and a 5 or 6 membered cycloheteroalkyl comprising 1 or 2 heteroatoms, each heteroatom being selected from oxygen, nitrogen and sulphur, $R_3$ represents an $OR_7$ group, $R_7$ being selected from:

hydrogen, and a linear or branched alkyl group comprising from 2 to 6 carbon atoms, and m and n are independently of each other an integer selected from 0 and 1.

6. The compound according to claim 1, wherein $R_1$ represents a linear or branched alkyl group comprising from 1 to 6 carbon atoms, substituted by a phenyl group, which is substituted by a phenyl group.

7. The compound according to claim 1, wherein $R_2$ represents a linear or branched alkyl group comprising from 1 to 6 carbon atoms, which is non-substituted or substituted by an aryl.

8. The compound according to claim 1, wherein $R_3$ represents an OH group.

9. The compound according to claim 1, wherein:

$R_1$=(R)—$CH_2$Ph-4-Ph; $R_2$=(S)—$CH_3$; $R_3$=OH; n=m=0;

$R_1$=(S)—$CH_2$Ph-4-Ph; $R_2$=(S)—$CH_3$; $R_3$=OH; n=m=0.

10. A pharmaceutical composition comprising at least one compound such as defined according to claim 1 and at least one pharmaceutically acceptable excipient.

11. The pharmaceutical composition according to claim 10 further comprising an analgesic selected from the group consisting of morphine and derivatives thereof, endocannabinoids and inhibitors of their metabolism, GABA derivatives, duloxetine or channel inhibitors.

12. A compound of following formula (II):

$$H-CO-N(OR)-CH_2-CH(R_1)-CO-NH-(CH_2)_n-CH(R_2)-(CH_2)_m-CO-R_3 \quad (II)$$

wherein:

R represents:

a linear or branched hydrocarbon group comprising from 1 to 6 carbon atoms non-substituted or substituted by one or more aryl groups themselves non-substituted or substituted by one or more groups selected from aryls and linear or branched alkyl groups comprising from 1 to 4 carbons, or a $Si(R_{10})_3$ group, $R_{10}$ being a linear or branched alkyl group comprising from 1 to 4 carbon atoms, $R_1$ represents a linear or branched hydrocarbon group comprising from 1 to 6 carbon atoms substituted by one or more groups selected from:

an aryl non-substituted or substituted by one or more groups selected from halogens, a phenyl group, a benzyl group, an $OR_4$ group, $R_4$ being selected from hydrogen and a linear or branched alkyl group comprising from 1 to 4 carbon atoms, and combinations thereof, a 5 or 6 membered heteroaryl comprising 1 or 2 heteroatoms, each heteroatom being selected from oxygen, nitrogen and sulphur, and a 5 or 6 membered cycloheteroalkyl comprising 1 or 2 heteroatoms, each heteroatom being selected from oxygen, nitrogen and sulphur, $R_2$ represents:

a linear or branched hydrocarbon group comprising from 1 to 6 carbon atoms, non-substituted or substituted by one or more groups selected from:

a group selected from ORS, $SR_5$ and $S(O)R_5$, $R_5$ being selected from hydrogen and a linear or branched alkyl group comprising from 1 to 4 carbons, a $CO_2R_6$ group, $R_6$ being selected from hydrogen, a linear or branched alkyl group comprising from 2 to 4 carbon atoms and a benzyl group, a 5 or 6 membered heteroaryl comprising 1 or 2 heteroatoms, each heteroatom being selected from oxygen, nitrogen and sulphur, a 5 or 6 membered cycloalkyl, and a 5 or 6 membered cycloheteroalkyl comprising 1 or 2 heteroatoms, each heteroatom being selected from oxygen, nitrogen and sulphur, or an aryl, non-substituted or substituted by one or more groups selected from halogens, an $OR_5$ group, $R_5$ having the same definition as above, and combinations thereof, or a heteroaryl comprising 1 or more heteroatoms, each heteroatom being selected from oxygen, nitrogen and sulphur, non-substituted or substituted by one or more groups selected from halogens, an $OR_5$ group, $R_5$ having the same definition as above, and combinations thereof, $R_3$ represents:

an $OR_7$ group, $R_7$ being selected from:

hydrogen, a linear or branched alkyl group comprising from 2 to 6 carbon atoms a benzyl group, and a $CHR_8$—$COOR_9$, $CHR_8$—O—C(═O)$R_9$ or $CHR_8$—O—C(═O)—$OR_9$ group wherein $R_8$ and $R_9$ are, independently of each other, selected from an alkyl group, an aryl group, an arylalkyl group, a cycloalkyl group, a cycloheteroalkyl group, a heteroalkyl group, a heteroaryl group and a heteroarylalkyl group, and m and n are independently of each other an integer selected from 0 and 1, the carbon atom bearing $R_1$ having an absolute configuration (R) or (S) and the carbon atom bearing $R_2$ having an absolute configuration (S), as well as pharmaceutically acceptable salts and/or solvates thereof.

13. A pharmaceutical composition comprising at least one compound of following formula (I) and at least one pharmaceutically acceptable excipient;

$$H—CO—N(OH)—CH_2—CH(R_1)—CO—NH—(CH_2)_n—CH(R_2)—(CH_2)_m—CO—R_3 \quad (I)$$

wherein:

$R_1$=(R)—$CH_2Ph$; $R_2$=(S)—$CH_3$; $R_3$=OH; n=m=0;
$R_1$=(S)—$CH_2Ph$; $R_2$=(S)—$CH_3$; $R_3$=OH; n=m=0;
$R_1$=(R)—$CH_2Ph$; $R_2$=(S)—$CH_2Ph$; $R_3$=OH; n=m=0;
$R_1$=(S)—$CH_2Ph$; $R_2$=(S)—$CH_2Ph$; $R_3$=OH; n=m=0;
$R_1$=(R)—$CH_2Ph$; $R_2$=(S)—$CH_2Ph$; $R_3$=OH: n=0; m=1;
$R_1$=(S)—$CH_2Ph$; $R_2$=(S)—$CH_3$; $R_3$=OH; n=0 m=1;
$R_1$=(R)—$CH_2Ph$-4-Ph; $R_2$=(S)—$CH_3$; $R_3$=OH; n=m=0;
$R_1$=(S)—$CH_2Ph$-4-Ph; $R_2$=(S)—$CH_3$; R=OH; n=m=0;
$R_1$=(S)—$CH_2Ph$; $R_2$=(S)—$CH_2Ph$; $R_3$=OH; n=1; m=0,
$R_1$=(R)—$CH_2Ph$; $R_2$=(S)—$CH_2Ph$; $R_3$=OH; n=1; m=0.

14. A method for treating pain comprising administering to a patient in need thereof an effective dose of the compound of formula (I) according to claim 1.

15. A method for treating pain comprising administering to a patient in need thereof an effective dose of the compound of formula (I) according to claim 9.

16. A method for treating pain comprising administering to a patient in need thereof an effective dose of the compound of formula (II) according to claim 12, provided that the R group in said compound of formula (II) is a labile group under physiological conditions.

17. A compound of following formula (I):

$$H—CO—N(OH)—CH_2—CH(R_1)—CO—NH—(CH_2)_n—CH(R_2)—(CH_2)_m—CO—R_3 \quad (I)$$

wherein:

$R_1$ is $CH_2Ph$,
$R_2$ is $CH_2Ph$,
$R_3$ is OH,
m=0, and
n=0.

* * * * *